(12) United States Patent
Inoue et al.

(10) Patent No.: US 6,231,539 B1
(45) Date of Patent: May 15, 2001

(54) BACKFLOW PREVENTION STRUCTURE AND A BACKFLOW PREVENTION UNIT FOR A LIQUID MEDICINE INJECTION DEVICE

(75) Inventors: Mitsuyoshi Inoue, Sakai; Yasuo Komatsu, Kokawa-cho; Atsushi Yamamoto, Kokubunji, all of (JP)

(73) Assignee: Daiken Iki Kabushiki Kaisha, Osaka (JP)

(*) Notice: Subject to any disclaimer, the term of this patent is extended or adjusted under 35 U.S.C. 154(b) by 0 days.

(21) Appl. No.: 09/499,346

(22) Filed: Feb. 8, 2000

(30) Foreign Application Priority Data

Feb. 10, 1999 (JP) .................................................. 11-033137
Jul. 23, 1999 (JP) .................................................. 11-208787
Nov. 19, 1999 (JP) .................................................. 11-329439

(51) Int. Cl.$^7$ ..................................................... A61M 1/00
(52) U.S. Cl. .......................................... 604/30; 604/246
(58) Field of Search ................................ 604/30, 34, 32, 604/33, 246, 247, 248, 249, 250

(56) References Cited

U.S. PATENT DOCUMENTS

| | | | | |
|---|---|---|---|---|
| 3,650,093 | * | 3/1972 | Rosenberg | 604/34 |
| 4,030,495 | * | 6/1977 | Virag | 128/214 |
| 4,114,617 | * | 9/1978 | Turner et al. | 128/214 |
| 4,871,353 | * | 10/1989 | Thomsen | 604/83 |

* cited by examiner

*Primary Examiner*—Manuel Mendez
(74) *Attorney, Agent, or Firm*—Smith Patent Office

(57) ABSTRACT

A backflow prevention structure, which is to be connected to a liquid medicine inlet of a liquid medicine injection device for injecting a liquid medicine in a liquid medicine retaining vessel of the liquid medicine injection device into a body part, includes a backflow prevention valve element provided at the liquid medicine inlet for preventing backflow of the liquid medicine from the liquid medicine retaining vessel. The backflow prevention valve element has a beaklike nonreturn valve and an annular valve and the liquid medicine is introduced into the liquid medicine retaining vessel through the beaklike nonreturn valve, and the liquid medicine in the liquid medicine retaining vessel is allowed to flow in a reverse direction via the annular valve when a negative pressure is produced on one side of the backflow prevention valve element opposite to the liquid medicine retaining vessel.

14 Claims, 14 Drawing Sheets

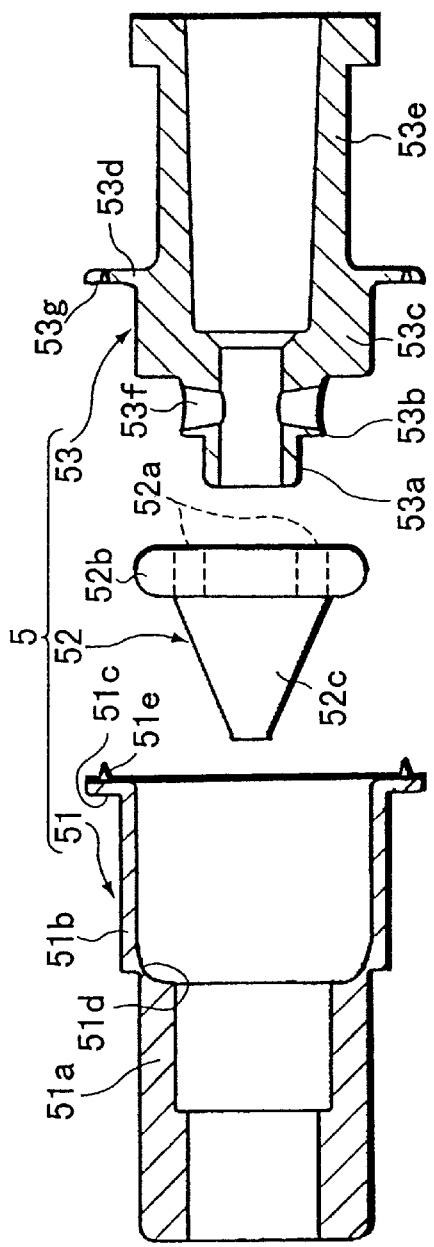
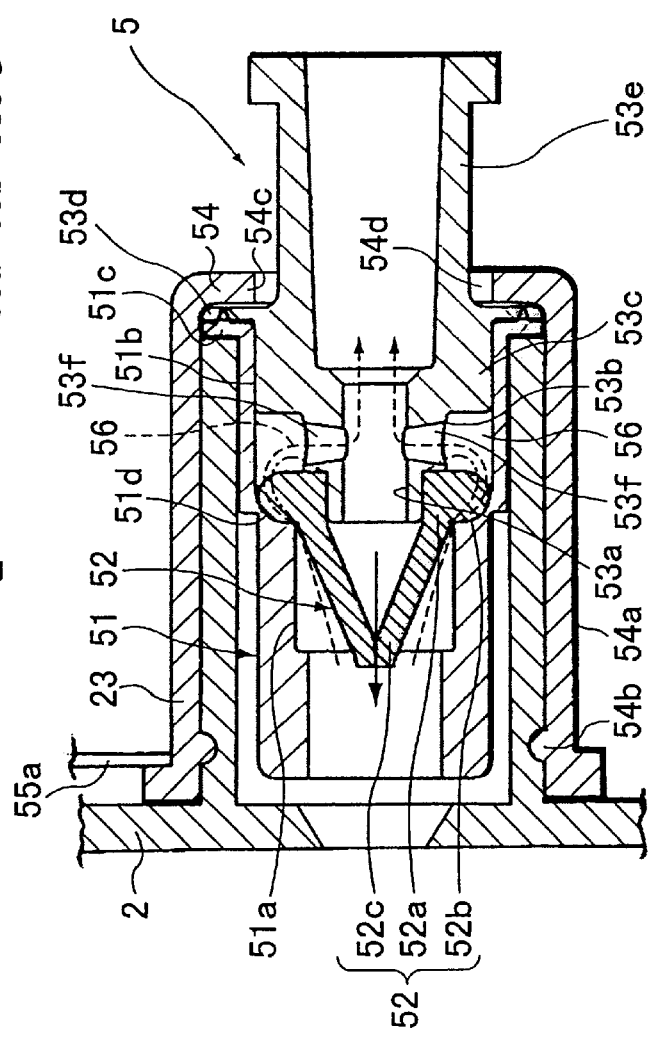
FIG. 7A
FIG. 7B

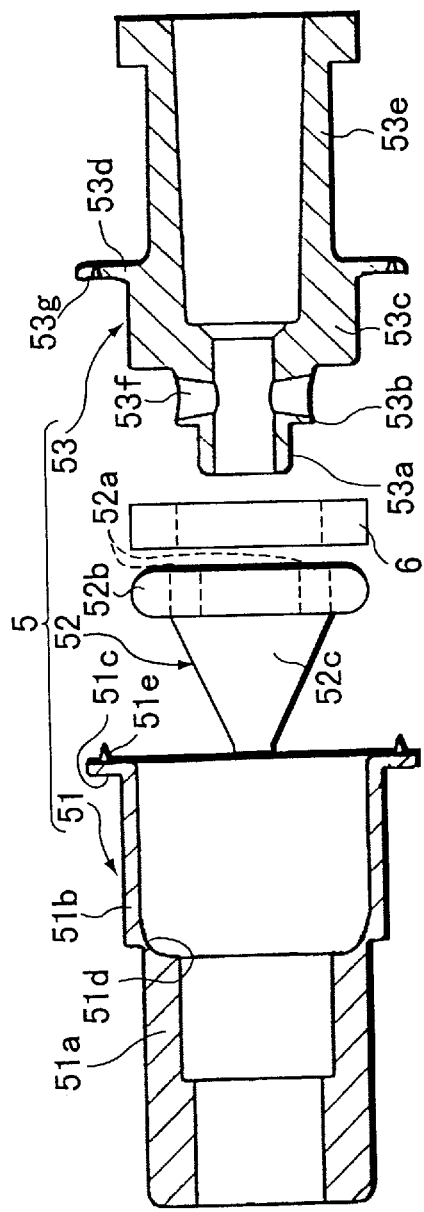
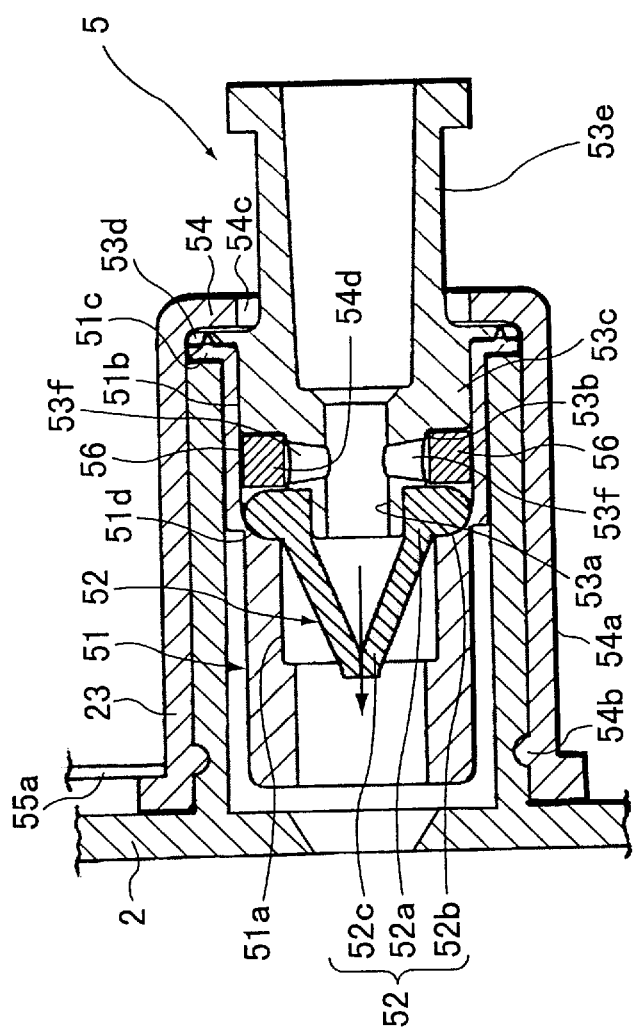
FIG.11A
FIG.11B

US 6,231,539 B1

BACKFLOW PREVENTION STRUCTURE AND A BACKFLOW PREVENTION UNIT FOR A LIQUID MEDICINE INJECTION DEVICE

This application is based on patent application Ser. Nos. 11-33137, 11-208787, and 11-329439 filed in Japan, the contents of which are hereby incorporated by references.

BACKGROUND OF THE INVENTION

This invention pertains generally to a liquid medicine injection device used in medical applications and, more particularly, relates to a backflow prevention structure and a backflow prevention unit for a liquid medicine injection device which allows easy liquid medicine filling operation.

FIGS. 14A and 14B illustrate an example of a conventional liquid medicine injection device 100, which comprises a liquid medicine retaining vessel 110 containing a liquid medicine to be injected, a backflow prevention structure 120 provided at an opening of the liquid medicine retaining vessel 110 at its one end (right end as shown in FIGS. 14A and 14B), and a tip cover 130 which closes off the opening of the liquid medicine retaining vessel 110.

The liquid medicine retaining vessel 110 accommodates in its internal space a piston 111 which can move back and forth in sliding contact, and has a connecting sleeve 112 whose diameter is smaller than that of the liquid medicine retaining vessel 110 itself at its right end. The aforementioned backflow prevention structure 120 is fitted in the connecting sleeve 112. The tip cover 130 Is constructed of a socket portion 131 which is fitted over the connecting sleeve 112 such that the socket portion 131 will not come off the connecting sleeve 112, and an inlet tube 132 which extends outward from a right end of the socket portion 131 and has a smaller diameter than the socket portion 131. The inlet tube 132 is provided for inserting an injection tube 210 of an injector 200 which has a cylinder 230 for holding the liquid medicine to be refilled into the liquid medicine retaining vessel 110 and a piston 220 for forcing the liquid medicine out of the cylinder 230.

The liquid medicine retaining vessel 110 also has an outlet tube 113 extending from a right end surface of the liquid medicine retaining vessel 110 for discharging the liquid medicine therein. With a delivery pipe 114 connected to the outlet tube 113, the liquid medicine within the liquid medicine retaining vessel 110 is forced out through the outlet tube 113 and introduced into a human body through the delivery pipe 114, a flow rate regulator and a catheter as the piston 111 is moved rightward by an unillustrated drive mechanism.

The aforementioned backflow prevention structure 120 includes a support cylinder 121 which is fitted into the connecting sleeve 112 such that a curved outer surface of the support cylinder 121 can slide along a curved inner surface of the connecting sleeve 112, and a check valve 125 made of an rubber-like elastic material which is fitted concentrically in the support cylinder 121. The support cylinder 121 is provided with a support bar 122 situated on a central axis of the support cylinder 121, and the check valve 125 is fitted over the support bar 122. A plurality of rodlike stoppers 123 radially project from a curved outer surface of the support bar 122. Outer ends of these stoppers 123 are fixed to a curved inner surface of the support cylinder 121 so that the support bar 122 is located on the central axis of the support cylinder 121.

Also, an annular projection 115 jutting inward is formed at a root end of the curved inner surface of the connecting sleeve 112. This annular projection 115 prevents the support cylinder 121 from entering the interior of the liquid medicine retaining vessel 110.

The aforementioned check valve 125 is constructed of a cylindrical portion 126 whose diameter is slightly smaller than the inner diameter of the support cylinder 121 and a conical valve portion 127 having a solid truncated circular cone shape formed at a far end (right end as illustrated in FIGS. 14A and 14B) of the cylindrical portion 126. A plurality of ribs 128 running parallel to an axial direction are formed on the cylindrical portion 126 at regular intervals around its curved outer surface, and liquid medicine passages 300 are formed between these ribs 128.

The conical valve portion 127 is shaped such that it comes in contact with a conical slope 133 formed where a curved inner surface of the socket portion 131 and a curved inner surface of the inlet tube 132 meet when the tip cover 130 is fitted on the connecting sleeve 112. This makes it possible to securely prevent the liquid medicine in the liquid medicine retaining vessel 110 from leaking through the backflow prevention structure 120. Furthermore, there is formed a slotted groove 127a, through which the liquid medicine flows, in a projecting end (right end as illustrated in FIGS. 14A and 14B) of the conical valve portion 127 across the diameter of the projecting end.

According to the liquid medicine injection device 100 thus constructed, the liquid medicine is injected into the liquid medicine retaining vessel 110 as follows. First, the injection tube 210 of the injector 200 charged with the liquid medicine is inserted into the inlet tube 132 until a tip end of the injection tube 210 pushes the projecting end of the conical valve portion 127 inward as shown in FIG. 14A. Since the check valve 125 made of the rubber-like elastic material is deformed consequently, the projecting end of the conical valve portion 127 is forced into an internal space of the socket portion 131 of the tip cover 130 as shown in FIG. 14B. As a result, the liquid medicine passages 300 are formed in the backflow prevention structure 120 as shown by thick arrows in FIG. 14B. When the piston 220 of the injector 200 is pushed into the cylinder 230 in this condition, the liquid medicine within the cylinder 230 is injected into the liquid medicine retaining vessel 110 through the injection tube 210, the slotted groove 127a in the conical valve portion 127 and the liquid medicine passages 300 formed in a gap between the curved outer surface of the cylindrical portion 126 and the curved inner surface of the support cylinder 121. As the liquid medicine is injected in this fashion, the piston 111 in the liquid medicine retaining vessel 110 is caused to retract (leftward as illustrated).

When injection of the liquid medicine into the liquid medicine retaining vessel 110 is completed, the injection tube 210 of the injector 200 is pulled out of the inlet tube 132. Then, the check valve 125 which has been elastically deformed extends, or returns to its original shape, so that the conical valve portion 127 of the check valve 125 comes back into contact with the conical slope 133 of the tip cover 130 and thereby closes an opening in the tip cover 130 as shown in FIG. 14B. Therefore, the liquid medicine once introduced into the liquid medicine retaining vessel 110 will never leak to its exterior through the inlet tube 132.

In the above-described conventional liquid medicine injection device 100, the injection tube 210 of the injector 200 is pulled out of the inlet tube 132 when interrupting the injection of the liquid medicine into the liquid medicine retaining vessel 110 halfway or when the injection of the liquid medicine has been completed. If the injection tube 210 is pulled out quickly in such cases, the liquid medicine left in the liquid medicine passages 300 may flow out backward to the exterior through a gap between the conical slope 133 of the tip cover 130 and the conical valve portion 127 of the check valve 125 before the check valve 125 which has been reduced in length due to elastic deformation returns to its original length.

To avoid such a leakage problem, it would be necessary to pull the cylinder 230 (leftward as illustrated in FIGS. 14A and 14B) while exerting a pushing force on the piston 220 and, then, slowly extract the injection tube 210 out of the inlet tube 132. Such work is considerably difficult and impractical, however.

Furthermore, if the pushing force exerted on the piston 220 of the injector 200 is reduced during the injection of the liquid medicine into the liquid medicine retaining vessel 110, the liquid medicine once introduced into the liquid medicine retaining vessel 110 will flow back into the cylinder 230 through the slotted groove 127a due to internal pressure of the liquid medicine retaining vessel 110. It is therefore necessary to maintain the pushing force on the piston 220 of the injector 200 while injecting the liquid medicine, which is inconvenient and bothersome.

SUMMARY OF THE INVENTION

It is an object of the invention to provide a backflow prevention structure and a backflow prevention unit which has overcome problems residing in the prior art.

It is another object of the invention to provide a backflow prevention structure and a backflow prevention unit which, when incorporated in a liquid medicine injection device, make it possible to easily interrupt or terminate injection of a liquid medicine into the liquid medicine injection device and withdraw the liquid medicine once introduced therein without causing leakage of the liquid medicine, while ensuring ease of liquid medicine filling operation using an injector.

It is still another object of the invention to provide a backflow prevention structure and a backflow prevention unit for a liquid medicine injection device which also make it possible to selectively prohibit operation for withdrawing the liquid medicine already introduced into the liquid medicine injection device.

According to an aspect of the invention, a backflow prevention structure is connected to a liquid medicine inlet of a liquid medicine injection device for injecting a liquid medicine in a hollow vessel of the liquid medicine injection device into a body part. The structure comprises a backflow prevention valve element provided at the liquid medicine inlet for preventing backflow of the liquid medicine from the hollow vessel. The backflow prevention valve element has a first valve for introducing the liquid medicine into the hollow vessel, and a second valve for allowing the liquid medicine in the hollow vessel to flow in a reverse direction via the second valve when a negative pressure is produced on one side of the backflow prevention valve element opposite to the hollow vessel.

According to another aspect of the invention, a backflow prevention unit to be connected in a liquid medicine carrying channel for injecting a liquid medicine into a body part comprises a support cylinder to be fitted into the liquid medicine carrying channel in tight contact with its curved inner surface. The support cylinder has a large-inner-diameter portion on an inflow side and an adjoining small-inner-diameter portion, and a backflow prevention valve element which is fitted into the support cylinder from its inflow side. The backflow prevention valve element has a cylindrical portion which is fitted into the large-inner-diameter portion of the support cylinder, a beaklike nonreturn valve which is formed integrally with the cylindrical portion and fitted into the small-inner-diameter portion of the support cylinder, and an annular valve bulging outward from around a curved outer surface of the cylindrical portion of the backflow prevention valve element. The outer diameter of the annular valve is larger than the diameter of the small-inner-diameter portion of the support cylinder. A slit which opens only when the liquid medicine flows in a normal direction is formed in the beaklike nonreturn valve. The annular valve is shaped such that it comes in contact with a ringlike stepped stage formed between the small-inner-diameter portion and the large-inner-diameter portion when the backflow prevention valve element is fitted into the small-inner-diameter portion. The annular valve elastically deforms, creating a gap between itself and a peripheral part of a liquid medicine inlet, when a negative pressure is produced on one side of the backflow prevention valve element opposite to the body part.

These and other objects, features and advantages of the present invention will become more apparent upon a reading of the following detailed description and accompanying drawings.

BRIEF DESCRIPTION OF THE DRAWINGS

FIGS. 5A and 5B are diagrams depicting the operation of the backflow prevention structure of the first example, wherein FIG. 5A shows a situation in which a liquid medicine is being injected from an injector into a liquid medicine retaining vessel, and FIG. 5B shows a situation in which the liquid medicine already injected into the liquid medicine retaining vessel is being withdrawn;

FIGS. 7A and 7B are cross-sectional views of the backflow prevention structure of FIG. 6. wherein FIG. 7A shows a situation immediately before a backflow prevention valve element is mounted, and FIG. 7B shows a situation after the backflow prevention valve element has been mounted in position;

FIGS. 11A and 11B are cross-sectional views of the backflow prevention structure of FIG. 10;

DETAILED DESCRIPTION OF THE PREFERRED EMBODIMENTS OF THE INVENTION

Figure 1:
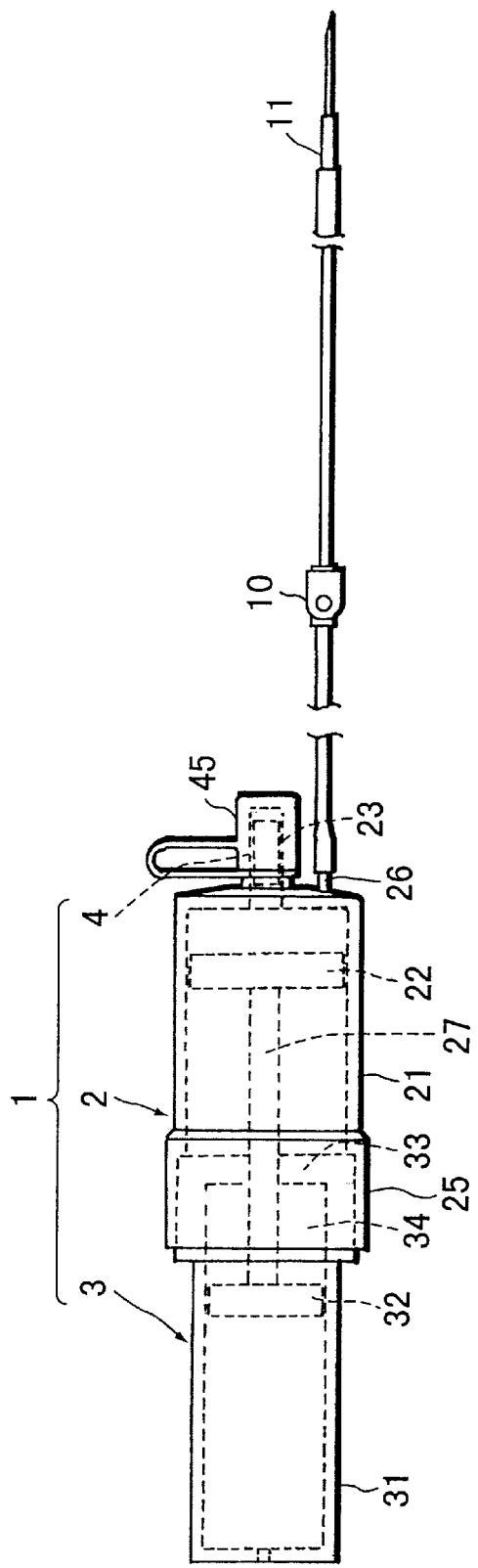
FIG. 1 is a diagram showing a liquid medicine injection device incorporating a backflow prevention unit according to a preferred embodiment of the invention.

FIG. 1 is a diagram showing a liquid medicine injection device 1 incorporating a backflow prevention unit according to a preferred embodiment of the invention. As shown in FIG. 1, the liquid medicine injection device 1 comprises as its basic constituent elements a liquid medicine retaining vessel 2 formed of a transparent synthetic resin material, a pump section 3 connected to one end (left end as illustrated) of the liquid medicine retaining vessel 2, and a backflow prevention structure 4 fitted in the other end of the liquid medicine retaining vessel 2. The liquid medicine retaining vessel 2 has a cylindrical retainer barrel 21, a first piston 22 which can move back and forth in the retainer barrel 21 with a curved outer surface of the first piston 22 held in sliding contact with a curved inner surface of the retainer barrel 21, and a connecting sleeve 23 projecting from a terminal end surface (right side) of the retainer barrel 21 on a common axis with it.

A later-described tip cover 43 which constitutes part of the backflow prevention structure 4 is tightly fitted over the aforementioned connecting sleeve 23. The tip cover 43 is provided with a removable cap 45. While the cap 45 is usually fitted on the tip cover 43, it is removed when injecting a liquid medicine into the retainer barrel 21. An outlet tube 26 extends outward from the terminal end surface of the retainer barrel 21. When the pump section 3 moves the first piston 22 rightward, the liquid medicine filled in the liquid medicine retaining vessel 2 is discharged through the outlet tube 26 and flows toward a flow rate regulator 10. Then, the liquid medicine whose flow rate has been regulated by the flow rate regulator 10 is introduced into a human body through a catheter 11.

A cylindrical mount portion 25 whose outer diameter is slightly larger than that of the retainer barrel 21 is formed as an integral part of the retainer barrel 21 at its left terminal end. The pump section 3 is fixed to the liquid medicine retaining vessel 2 as a terminal portion of the pump section 3 is fitted into the mount portion 25 and secured therein by a fastener.

The pump section 3 has a pump cylinder 31 and a second piston 32 which is fitted in the pump cylinder 31 such that the second piston 32 can move back and forth in sliding contact with the pump cylinder 31. The second piston 32 and the aforementioned first piston 22 are connected to each other by a piston rod 27. The pump cylinder 31 has at its right terminal end opening an end wall 33, and the piston rod 27 passes through the end wall 33 in sliding contact. A vacuum chamber 34 is formed in the pump cylinder 31 just between the end wall 33 and the second piston 32.

In the liquid medicine injection device 1 thus constructed, when injection pressure is applied to inject the liquid medicine into the liquid medicine retaining vessel 2 through the backflow prevention structure 4 fitted to the connecting sleeve 23 with the flow rate regulator 10 closed off, the first piston 22 moves leftward due to the injection pressure so that the liquid medicine is injected into the liquid medicine retaining vessel 2. Since the second piston 32 also moves leftward as it is pressed by the piston rod 27 at this time, the degree of vacuum within the vacuum chamber 34 in the pump section 3 gradually increases. As will be explained later in detail, the liquid medicine once introduced into the liquid medicine retaining vessel 2 will never flow in a reverse direction through the connecting sleeve 23 due to the backflow prevention structure 4.

When the flow rate regulator 10 is opened in this condition, the second piston 32 moves rightward inside the pump cylinder 31 of the pump section 3 due to the high degree of vacuum within the vacuum chamber 34. Since the first piston 22 also moves rightward, the liquid medicine in the liquid medicine retaining vessel 2 is discharged through the outlet tube 26. The liquid medicine of which flow rate has been regulated by the flow rate regulator 10 is injected into the human body through the catheter 11.

Figure 2:
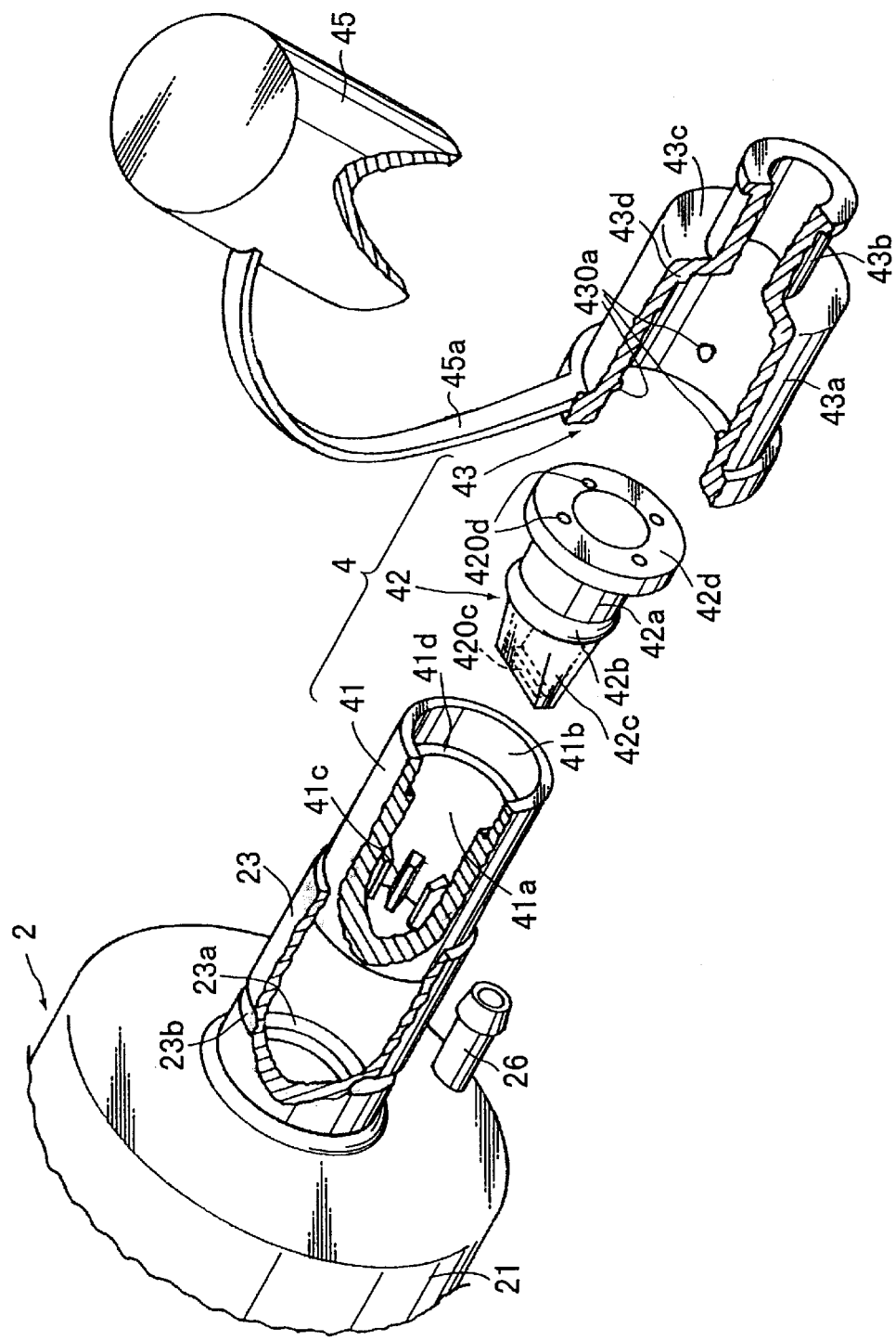
FIG. 2 is a partially cutaway exploded perspective view of a backflow prevention structure shown as a first example.
Figure 3:
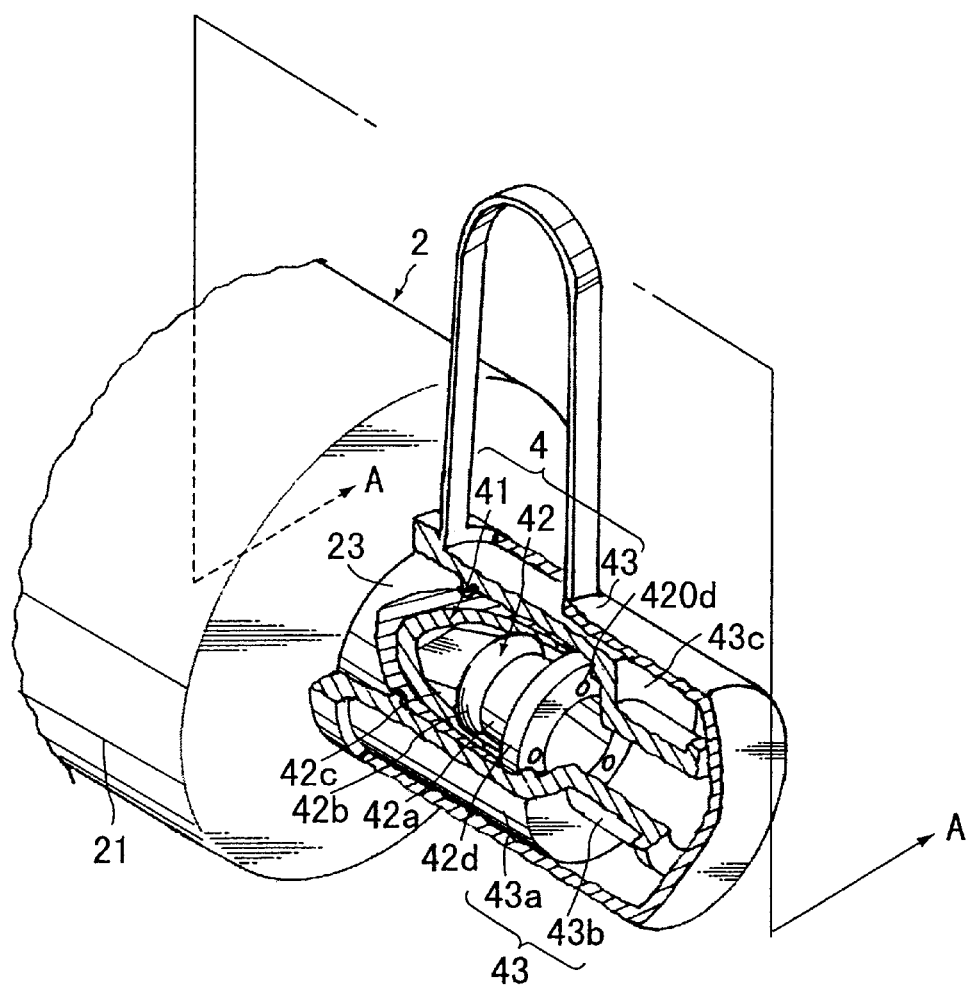
FIG. 3 is a perspective assembly diagram of the backflow prevention structure of FIG. 3.
Figure 4:
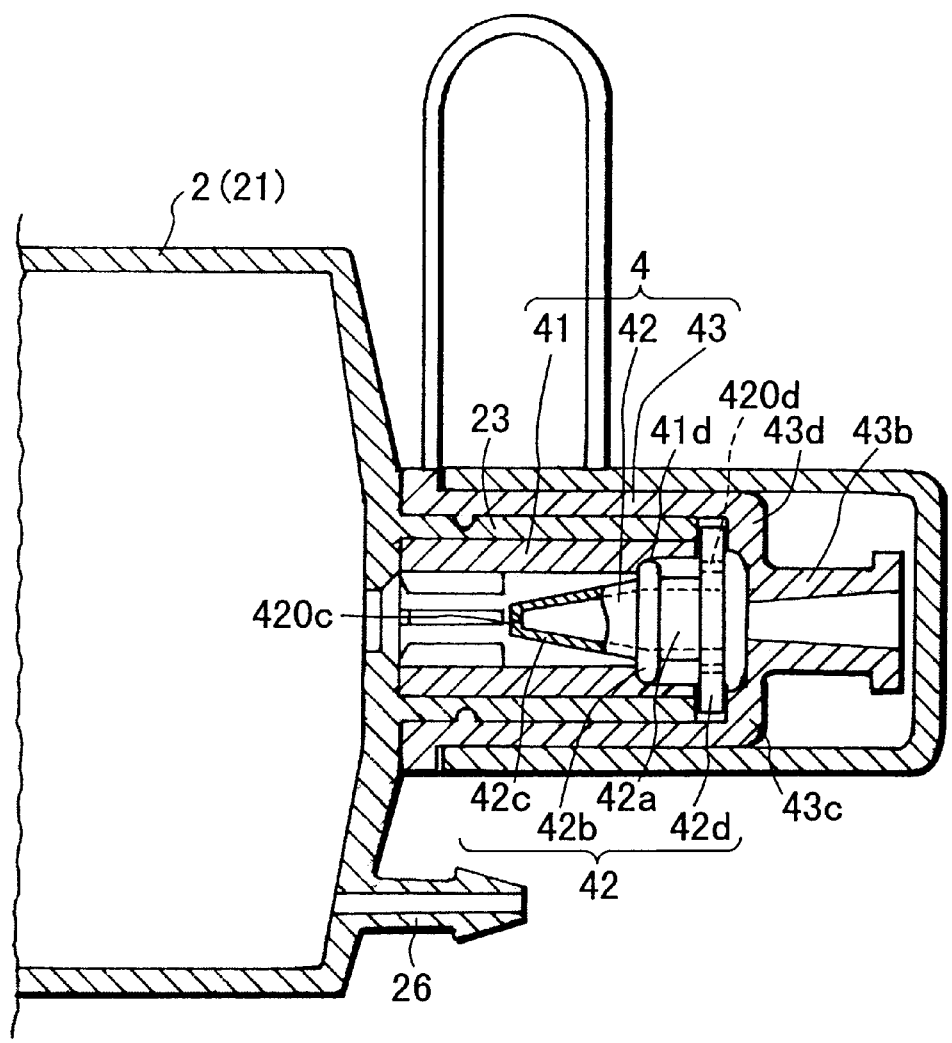
FIG. 4 is a cross-sectional view taken along lines A—A of FIG. 3.

FIG. 2 is a partially cutaway exploded perspective view of a backflow prevention structure 4 shown as a first example, FIG. 3 is its perspective assembly diagram, and FIG. 4 is a cross-sectional view taken along lines A—A of FIG. 3. As shown in these Figures, the backflow prevention structure 4 includes a support cylinder 41 which is fitted over the connecting sleeve 23, a backflow prevention valve element 42 which is mounted in the support cylinder 41, and the aforementioned tip cover 43 which is tightly fitted over the connecting sleeve 23.

The outer diameter of the support cylinder 41 is made slightly smaller than the inner diameter of the connecting sleeve 23 so that the support cylinder 41 can be fitted in the connecting sleeve 23 in sliding contact. The support cylinder 41 has a small-inner-diameter portion 41a which has a specific inner diameter and extends from a terminal end (left end as illustrated in FIG. 2) of the support cylinder 41 toward its opposite root end, and a large-inner-diameter portion 41b which has a larger inner diameter than the small-inner-diameter portion 41a and extends from the small-inner-diameter portion 41a up to the root end of the support cylinder 41.

A plurality of ribs 41c running parallel to a longitudinal axis of the support cylinder 41 are formed on a curved inner surface of the small-inner-diameter portion 41a from its terminal end (left end). The ribs 41c are arranged at regular angular intervals on the curved inner surface of the small-inner-diameter portion 41a and protrude inward therefrom toward the longitudinal axis of the support cylinder 41. These ribs 41c serve to give structural strength to the support cylinder 41.

There is formed a ringlike arc-shaped stepped stage 41d at a terminal end (left end as illustrated in FIG. 2) of the large-inner-diameter portion 41b. The ringlike arc-shaped stepped stage 41d is arc-shaped in cross section and serves to hold the backflow prevention valve element 42 in position. The support cylinder 41 thus constructed has approximately the same length as the connecting sleeve 23. There is formed a ringlike projection 23a protruding inward from a curved inner surface of the connecting sleeve 23 at its root portion. The ringlike projection 23a prevents the support cylinder 41 which has been fitted into the connecting sleeve 23 from entering further inward. There is also formed a ringlike groove 23b for retaining the tip cover 43 in a curved outer surface of the connecting sleeve 23 at its root portion.

The backflow prevention valve element 42 of this example is made of silicone rubber which is a rubber-like elastic material. The backflow prevention valve element 42 has a cylindrical portion 42a whose outer diameter is approximately equal to the inner diameter of the small-inner-diameter portion 41a of the support cylinder 41, an annular valve (second valve) 42b bulging radially outward in a doughnut shape from all around a left terminal end of the cylindrical portion 42a (as illustrated in FIGS. 2–4), a beaklike nonreturn valve (first valve) 42c extending from a left terminal end of the annular valve 42b, and a flange 42d which is formed at a right terminal end of the cylindrical portion 42a (as illustrated in FIGS. 2–4) and has a slightly smaller outer diameter than the connecting sleeve 23.

The annular valve 42b has an arc-shaped cross section whose curvature is the same as the cross-sectional shape of the ringlike arc-shaped stepped stage 41d. Therefore, when the backflow prevention valve element 42 is inserted into the support cylinder 41, a curved outer surface of the annular valve 42b comes in tight contact with a curved surface of the ringlike arc-shaped stepped stage 41d as shown in FIG. 4, and as a consequence, free passage between the small-inner-diameter portion 41a and the large-inner-diameter portion 41b of the support cylinder 41 is cut.

The total length of the cylindrical portion 42a and the annular valve 42b of the backflow prevention valve element 42 is made equal to the length of the large-inner-diameter portion 41b of the support cylinder 41 as measured in its longitudinal direction. Therefore, when the backflow prevention valve element 42 is inserted into the support cylinder 41, the flange 42d rests on a circular edge of the support cylinder 41 on its inflow side.

The beaklike nonreturn valve 42c is tapered toward its end like a bird beak. There is formed a slit 420c in a narrowed end surface of the beaklike nonreturn valve 42c. While the liquid medicine introduced into the backflow prevention valve element 42 from its upstream side (right side as illustrated in FIGS. 2–4) can flow into the liquid medicine retaining vessel 2 through the slit 420c, the liquid medicine already introduced into the liquid medicine retaining vessel 2 can not open the slit 420c and this prohibits backflow of the liquid medicine from the liquid medicine retaining vessel 2 into the backflow prevention valve element 42.

The flange 42d of the backflow prevention valve element 42 has a plurality of bypass holes 420d formed at regular intervals on a circle. These bypass holes 420d are formed slightly outside of a curved outer surface of the cylindrical portion 42a of the backflow prevention valve element 42. Therefore, when the backflow prevention valve element 42 is inserted into the support cylinder 41, the bypass holes 420d connect to a ringlike passage 44 formed between a curved inner surface of the large-inner-diameter portion 41b and the curved outer surface of the cylindrical portion 42a as shown in FIG. 4.

With the backflow prevention valve element 42 inserted into the support cylinder 41, the tip cover 43 is fitted over the connecting sleeve 23 as shown in FIG. 4, whereby the backflow prevention valve element 42 is prohibited from coming off accidentally. The tip cover 43 is constructed of a cylindrical socket portion 43a which is fitted over the connecting sleeve 23 in sliding contact and an inlet tube 43b which extends from an upstream end (right side as illustrated in FIGS. 2–4) of the socket portion 43a. A through hole in the inlet tube 43b is tapered such that its inner diameter gradually decreases from its upstream side (right side as illustrated in FIGS. 2–4) to downstream side.

There are formed a plurality of snap-on projections 430a on a curved inner surface of the socket portion 43a at regular intervals in its circumferential direction. These snap-on projections 430a are made at positions corresponding to the ringlike groove 23b formed in the connecting sleeve 23. Thus, when the tip cover 43 is fitted over the connecting sleeve 23, the snap-on projections 430a fit in the ringlike groove 23b and, as a consequence, the tip cover 43 is prohibited from coming off accidentally.

The socket portion 43a and the inlet tube 43b of the tip cover 43 are connected to each other by a disklike end wall 43c, which has a ringlike projection 43d formed all along a circular corner where an inner surface of the disklike end wall 43c intersects the curved inner surface of the socket portion 43a. The inner diameter of the ringlike projection 43d is made approximately equal to that of the large-inner-diameter portion 41b of the support cylinder 41. The physical size of the tip cover 43 is determined such that the ringlike projection 43d presses against a peripheral part of the flange 42d of the backflow prevention valve element 42 when the tip cover 43 is fitted over the connecting sleeve 23. The aforementioned ringlike passage 44 formed between the curved inner surface of the large-inner-diameter portion 41b and the curved outer surface of the cylindrical portion 42a passes the liquid medicine when the tip cover 43 is fitted over the connecting sleeve 23 (FIG. 4). The ringlike passage 44 is used when flowing the liquid medicine in the reverse direction through the backflow prevention valve element 42.

The backflow prevention valve element 42 is not elastically deformed by pressure of the liquid medicine already injected into the liquid medicine retaining vessel 2 when the annular valve 42b is forced against the ringlike arc-shaped stepped stage 41d of the support cylinder 41 in this invention. However, the backflow prevention valve element 42 has appropriate elasticity such that, when suction is applied developing a negative pressure in the ringlike passage 44, the backflow prevention valve element 42 will be elastically deformed toward a negative pressure side due to an increase in pressure difference.

As thus far described, the support cylinder 41 in which the backflow prevention valve element 42 has been inserted is fitted into the connecting sleeve 23 and the tip cover 43 is fitted over the connecting sleeve 23 in the backflow prevention structure 4 of this first example. If the liquid medicine is introduced with pressure through the inlet tube 43b, the liquid medicine flows through the backflow prevention valve element 42, opening the slit 420c in the beaklike nonreturn valve 42c, and is delivered into the liquid medicine retaining vessel 2.

On the contrary, If a suction force is applied to the backflow prevention structure 4 with a specific suction jig connected to the inlet tube 43b, a negative pressure is produced in the ringlike passage 44 within the support cylinder 41. As a consequence, the annular valve 42b elastically deforms, creating a gap between the annular valve 42b and the ringlike arc-shaped stepped stage 41d, so that the liquid medicine in the liquid medicine retaining vessel 2 is drawn into the ringlike passage 44 through this gap and discharged to the exterior through the bypass holes 420d and the inlet tube 43b.

The aforementioned cap 45 is affixed to the tip cover 43 by a connecting band 45a. Although the cap 45 is usually fitted on the socket portion 43a as shown in FIG. 3, it is removed when injecting the liquid medicine into the liquid medicine retaining vessel 2.

Figure 5A:
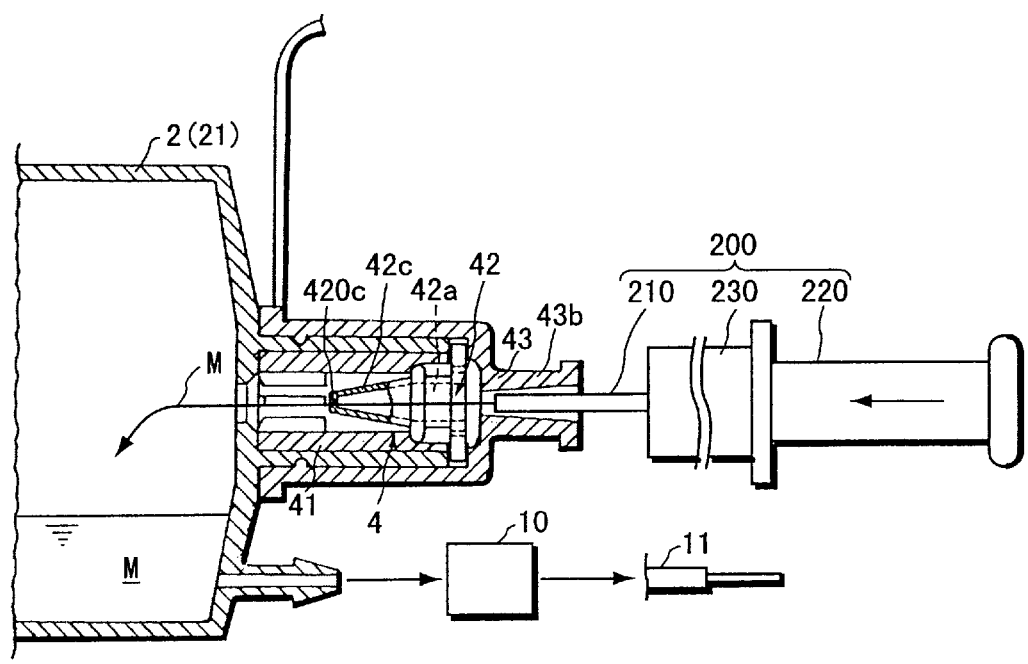
Figure 5B:
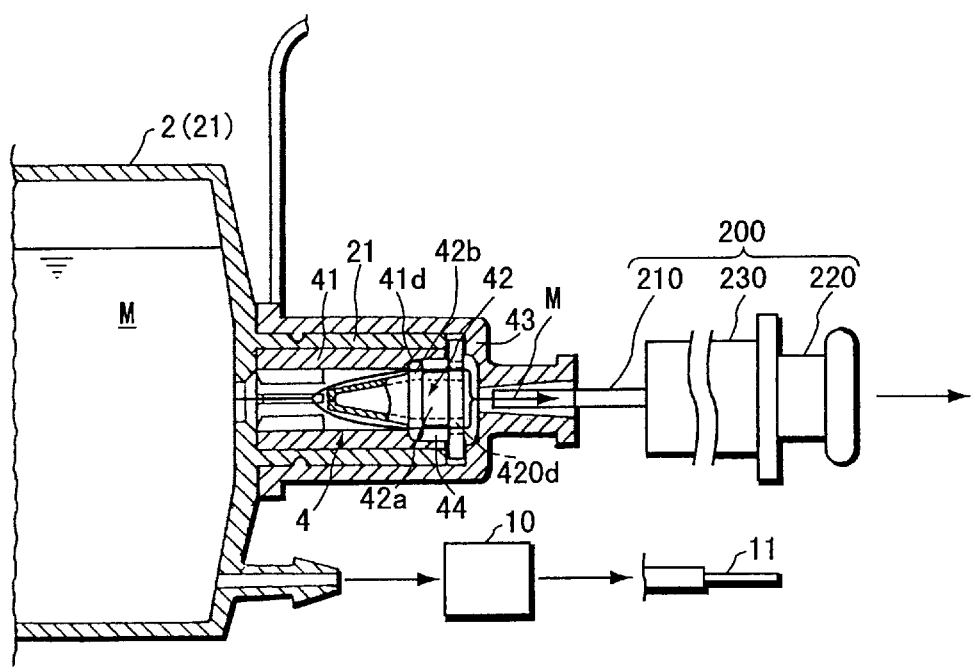

FIGS. 5A and 5B are diagrams depicting the operation of the backflow prevention structure 4 of the first example, wherein FIG. 5A shows a situation in which the liquid medicine is being injected from an injector 200 into the liquid medicine retaining vessel 2, and FIG. 5B shows a situation in which the liquid medicine already injected into the liquid medicine retaining vessel 2 is being withdrawn.

When injecting the liquid medicine M into the liquid medicine retaining vessel 2, a piston 220 is pushed leftward with an injection tube 210 of the injector 200 inserted into the inlet tube 43b as shown in FIG. 5A. As the piston 220 is pushed into a cylinder 230, the liquid medicine M which has been filled in the cylinder 230 is forced out from a tip end of the injection tube 210. The liquid medicine M then passes through the cylindrical portion 42a and the beaklike nonreturn valve 42c of the backflow prevention valve element 42 and, while forcing the slit 420c in the end surface of the beaklike nonreturn valve 42c open, flows into the support cylinder 41 and is injected into the liquid medicine retaining vessel 2. A specified amount of the liquid medicine M thus introduced into the liquid medicine retaining vessel 2 does not flow in the reverse direction even when the injection tube 210 is removed from the inlet tube 43b, because backflow of the liquid medicine M is prohibited by the backflow prevention valve element 42.

Occasionally, however, the liquid medicine M could be overfilled Into the liquid medicine retaining vessel 2 due to an operational error, for example. In such cases, it is necessary to withdraw the liquid medicine M once injected into the liquid medicine retaining vessel 2. This is achieved by inserting the injection tube 210 of the injector 200 into the inlet tube 43b of the tip cover 43 and pulling the piston 220 (rightward as illustrated in FIGS. 5A and 5B) with a tip end of the injection tube 210 forced against an inner surface of the inlet tube 43b. This develops a negative pressure in the inlet tube 43b, causing the annular valve 42b to be deformed toward its upstream side (rightward as illustrated). Since a gap is created between the curved outer surface of the annular valve 42b and the ringlike arc-shaped stepped stage 41d due to the deformation of the annular valve 42b, the liquid medicine M is drawn into the Inlet tube 43b through this gap, the ringlike passage 44 and the bypass holes 420d and recovered into the cylinder 230, as shown in FIG. 5B.

As thus far described in detail, the backflow prevention structure 4 of the first example is constructed of the support cylinder 41, the backflow prevention valve element 42 and the tip cover 43, and the tip cover 43 is fitted over the connecting sleeve 23 after inserting the support cylinder 41, in which the backflow prevention valve element 42 has been fitted, into the connecting sleeve 23. This construction makes it possible to dispose the backflow prevention structure 4 as if it is formed in a liquid medicine inlet of the liquid medicine retaining vessel 2.

Since the backflow prevention valve element 42 is made of the cylindrical portion 42a, the annular valve 42b formed immediately downstream of the cylindrical portion 42a, the beaklike nonreturn valve 42c formed immediately downstream of the annular valve 42b and the flange 42d formed upstream of the cylindrical portion 42a, and the support cylinder 41 has the small-inner-diameter portion 41a, in which the beaklike nonreturn valve 42c is fitted, and the large-inner-diameter portion 41b associated with the ringlike arc-shaped stepped stage 41d where the flange 42d is seated, the beaklike nonreturn valve 42c is positioned in the small-inner-diameter portion 41a and the annular valve 42b comes into contact with the ringlike arc-shaped stepped stage 41d when the backflow prevention valve element 42 is inserted into the support cylinder 41. The beaklike nonreturn valve 42c and the annular valve 42b work together to prevent backflow of the liquid medicine.

Furthermore, since the backflow prevention structure 4 is constructed such that a gap is created between the curved outer surface of the annular valve 42b and the curved inner surface of the large-inner-diameter portion 41b due to the deformation of the annular valve 42b when a negative pressure is produced upstream of the backflow prevention valve element 42, it is possible to recover the liquid medicine in the liquid medicine retaining vessel 2 back into the cylinder 230 of the injector 200 through the annular valve 42b by fitting the injection tube 210 of the injector 200 into the inlet tube 43b and pulling the piston 220 when the liquid medicine retaining vessel 2 has been overfilled with the liquid medicine, for example. This construction helps increase labor efficiency when It Is required to inject a specified amount of the liquid medicine into the liquid medicine retaining vessel 2.

Figure 6:
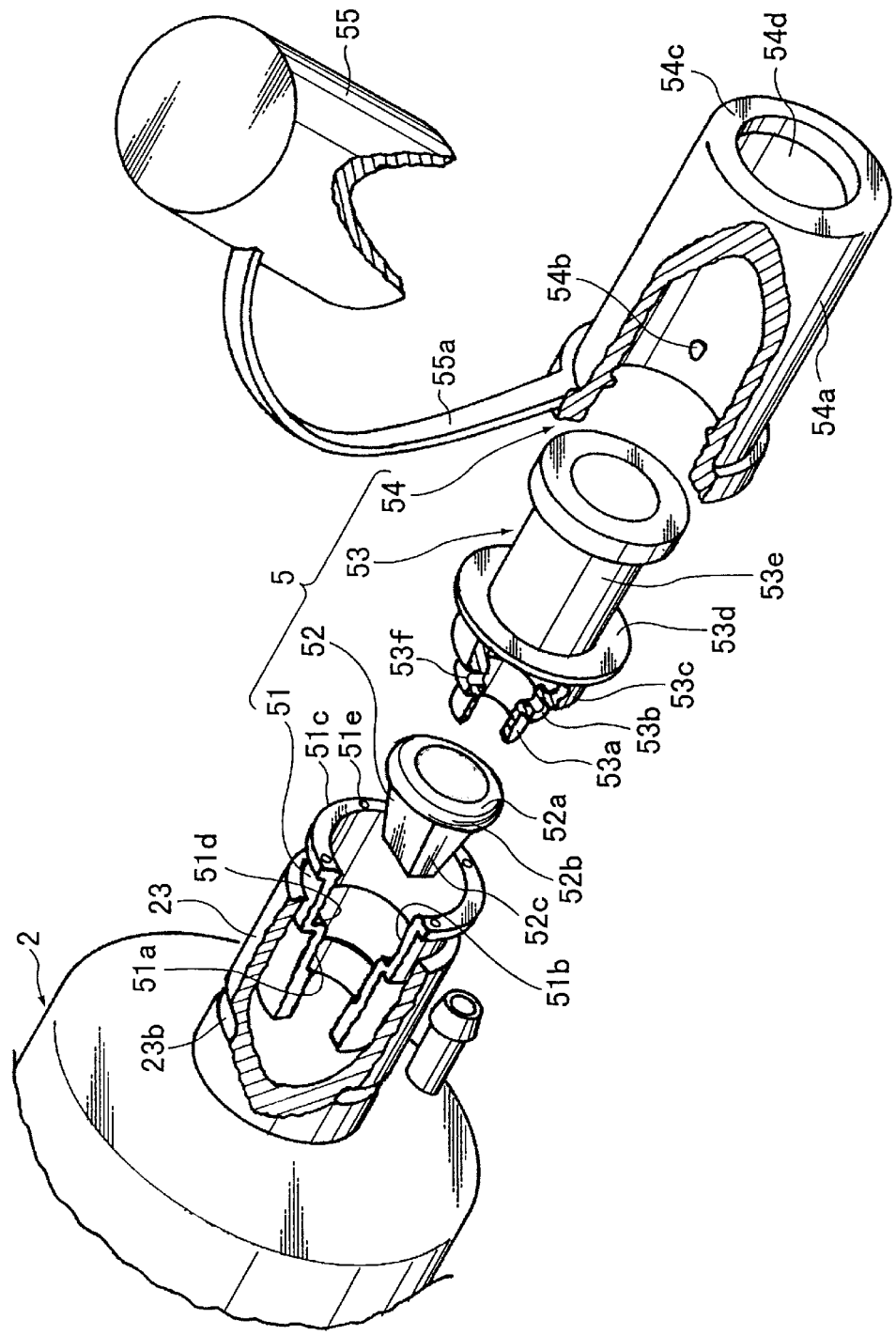
FIG. 6 is a partially cutaway exploded perspective view of a backflow prevention structure shown as a second example.

FIG. 6 is a partially cutaway exploded perspective view of a backflow prevention structure 5 shown as a second example, and FIGS. 7A and 7B are cross-sectional views of the backflow prevention structure 5 of FIG. 6, wherein FIG. 7A shows a situation immediately before a backflow prevention valve element 52 is mounted, and FIG. 7B shows a situation after the backflow prevention valve element 52 has been mounted in position.

In this second example, the backflow prevention structure 5 is includes a support cylinder 51 which is fitted over a connecting sleeve 23 of a liquid medicine retaining vessel 2, the backflow prevention valve element 52 which is mounted in the support cylinder 51, a valve retaining plug (valve retainer) 53 which is fitted into the support cylinder 51 to hold the backflow prevention valve element 52 in its correct mounting position, and a tip cover 54 which is constructed generally in the same fashion as the tip cover 43 of the aforementioned first example and fitted over the connecting sleeve 23 to prevent the valve retaining plug 53 from coming off.

Like the support cylinder 41 of the first example, the support cylinder 51 has a small-inner-diameter portion 51a and a large-inner-diameter portion 51b. The large-inner-diameter portion 51b has along its boundary with the small-inner-diameter portion 51a a ringlike arc-shaped stepped stage 51d similar to the ringlike arc-shaped stepped stage 41d of the first example. The support cylinder 51 also has a circular flangelike projection 51c which protrudes radially from all around the periphery of an inlet end of the large-inner-diameter portion 51b. The outer diameter of the circular flangelike projection 51c is made slightly smaller than that of the connecting sleeve 23. Therefore, when the support cylinder 51 is inserted into the connecting sleeve 23, the circular flangelike projection 51c comes in contact with an end surface of the connecting sleeve 23, and this prevents the support cylinder 51 from entering further into the connecting sleeve 23.

The backflow prevention valve element 52 is constructed as if by removing the flange 42d from the backflow prevention valve element 42 of the first example and reducing the length of the cylindrical portion 42a. Specifically, the backflow prevention valve element 52 has a cylindrical portion 52a, an annular valve 52b bulging radially outward from all around a curved outer surface of the cylindrical portion 52a to form a semicircular cross-sectional shape, and a beaklike nonreturn valve 52c extending from the cylindrical portion 52a toward the support cylinder 51 (as illustrated in FIG. 6). The beaklike nonreturn valve 52c is formed in exactly the same shape as the beaklike nonreturn valve 42c of the first example.

In the backflow prevention valve element 52, the thickness of the cylindrical portion 52a is made equal to that of the annular valve 52b as measured along their inner hole axis and the flange 42d is eliminated. The construction of the backflow prevention valve element 52 is therefore simplified compared to the backflow prevention valve element 42 of the first example. This makes it possible to produce the backflow prevention valve element 52 of the second example at a lower production cost than the backflow prevention valve element 42 of the first example.

The outer diameter of the annular valve 52b is made slightly smaller than the inner diameter of the large-inner-diameter portion 51b. Therefore, when the backflow prevention valve element 52 is inserted all the way into the large-inner-diameter portion 51b of the support cylinder 51, the annular valve 52b comes in contact with the ringlike arc-shaped stepped stage 51d, thereby prohibiting backflow of the liquid medicine from the liquid medicine retaining vessel 2.

The valve retaining plug 53 has a tubular connecting portion 53a whose outer diameter is slightly larger than the inner diameter of the cylindrical portion 52a of the backflow prevention valve element 52, a cylindrical pressing portion 53b whose outer diameter is approximately equal to that of the cylindrical portion 52a of the backflow prevention valve element 52, a cylindrical plug portion (plug portion) 53c whose outer diameter is determined such that it can be fitted in the large-inner-diameter portion 51b of the support cylinder 51 in sliding contact, a flange 53d formed around an upstream end of the cylindrical plug portion 53c, and an upstream cylindrical portion 53e extending upstream (rightward as illustrated in FIGS. 6, 7A and 7B) from the flange 53d. The outer diameter of the flange 53d is made approximately equal to that of the circular flangelike projection 51c of the support cylinder 51.

There are formed a plurality of radially extending bypass holes 53f in the cylindrical pressing portion 53b at regular intervals in its circumferential direction. Further, a plurality of retaining projections 51e are formed on a surface of the circular flangelike projection 51c facing the flange 53d at regular intervals on a circle while the same number of retaining holes 53g are formed in the flange 53d of the valve retaining plug 53 at positions corresponding to the individual retaining projections 51e.

Accordingly, when the beaklike nonreturn valve 52c of the backflow prevention valve element 52 is fitted in the small-inner-diameter portion 51a of the support cylinder 51 and the cylindrical plug portion 53c of the valve retaining plug 53 is inserted into the large-inner-diameter portion 51b of the support cylinder 51 in the situation shown in FIG. 7A, the tubular connecting portion 53a of the valve retaining plug 53 fits in a central cavity of the cylindrical portion 52a of the backflow prevention valve element 52, a side surface of the cylindrical portion 52a comes in contact with the cylindrical pressing portion 53b of the valve retaining plug 53, and the backflow prevention valve element 52 and the valve retaining plug 53 are mounted in the support cylinder 51 with the retaining projections 51e fitted in their corresponding retaining holes 53g as shown in FIG. 7B.

The tip cover 54 has basically the same construction as the tip cover 43 of the first example. Specifically, the tip cover 54 has a cylindrical socket portion 54a and a cap 55 which is affixed to the socket portion 54a by a connecting band 55a. Although the tip cover 54 also has snap-on projections 54a formed on a curved inner surface of the socket portion 54a to fit in a ringlike groove 23b in the connecting sleeve 23, there is no provision corresponding to the inlet tube 43b of the first example, so that the tip cover 54 has the same diameter all along its length except for its terminal end where the connecting band 55a is attached.

Instead of the inlet tube 43b, however, there is made a manipulation hole 54d in a bottom plate 54c of the socket portion 54a in this second example. This manipulation hole 54d allows an operator to manipulate the backflow prevention structure 5 when injecting the liquid medicine into the liquid medicine retaining vessel 2. In this tip cover 54, the diameter of the manipulation hole 54d is made larger than the outer diameter of an upstream end of the upstream cylindrical portion 53e of the valve retaining plug 53, and the length of a curved inner surface of the socket portion 54a is made equal to the sum of the length of the connecting sleeve 23 and the thicknesses of the circular flangelike projection 51c and the flange 53d.

Therefore, when the tip cover 54 is fitted over the connecting sleeve 23 with the cylindrical plug portion 53c of the valve retaining plug 53 fitted in the large-inner-diameter portion 51b of the support cylinder 51, the bottom plate 54c of the tip cover 54 comes in contact with the flange 53d of the valve retaining plug 53 as shown in FIG. 7B, whereby the backflow prevention structure 5 is mounted in the connecting sleeve 23 such that the backflow prevention structure 5 will not come off accidentally.

According to the backflow prevention structure 5 of the second example, when the liquid medicine is injected with an injection tube of an injector inserted into the cylindrical plug portion 53c of the valve retaining plug 53 through its upstream cylindrical portion 53e, the liquid medicine is introduced into the liquid medicine retaining vessel 2 through a slit formed in a narrowed end surface of the beaklike nonreturn valve 52c of the backflow prevention valve element 52 as shown by thick an arrow in FIG. 7B. On the contrary, when a negative pressure is produced in the valve retaining plug 53, the annular valve 52b elastically deforms toward its upstream side as shown by alternate long and two short dashed lines in FIG. 7B creating a gap between the annular valve 52b and the ringlike arc-shaped stepped stage 51d of the support cylinder 51 and, as a consequence, the liquid medicine in the liquid medicine retaining vessel 2 flows in a reverse direction through this gap, a backflow passage 56 and the bypass holes 53f in the cylindrical pressing portion 53b of the valve retaining plug 53 as shown by thick broken lines in FIG. 7B.

It would be appreciated from the foregoing discussion that the backflow prevention structure 5 of the second example provides the same advantageous effects as the backflow prevention structure 4 of the first example. Moreover, since the backflow prevention valve element 52 has a simplified construction without the provision of the flange 42d which is provided in the backflow prevention valve element 42 of the first example, for instance, it becomes possible to reduce the production cost of the backflow prevention valve element 52 which is a consumable. This construction is also advantageous in reducing the cost of maintenance of the liquid medicine injection device 1.

Figure 8:
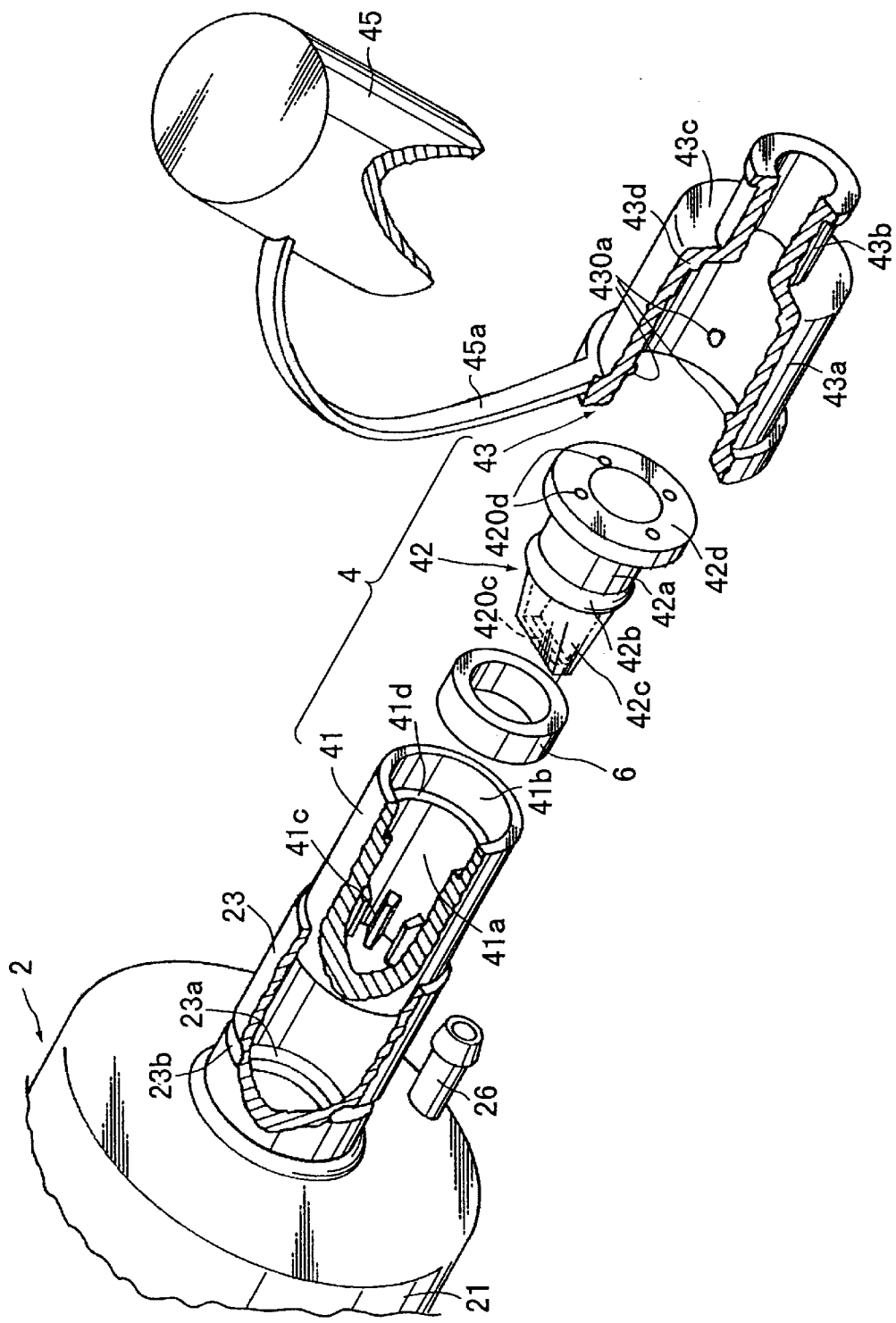
FIG. 8 is a partially cutaway exploded perspective view showing a variation of the backflow prevention structure of the first example shown in FIGS. 2–4.

FIG. 8 is a partially cutaway exploded perspective view showing a variation of the backflow prevention structure 4 of the first example shown in FIGS. 2–4, and FIG. 9 is a cross-sectional view of the backflow prevention structure 4 of FIG. 8. Although the basic construction of the backflow prevention structure 4 of this variation is same as that of the first example, the backflow prevention structure 4 of the variation makes it impossible to withdraw the liquid medicine once injected into the liquid medicine retaining vessel 2 even when an attempt is made to do so by using an as shown in FIG. 5B.

A reason why the backflow prevention structure 4 of this varied form is used in certain cases is as follows. Basically, the present invention provides a small-sized portable liquid medicine injection device 1. It is therefore is used not only in hospitals and other medical institutions but also in home medical care where the liquid medicine injection device 1 is usually operated by a patient or a family member of the patient. If the patient is allowed to withdraw the liquid medicine out of the liquid medicine retaining vessel 2, there can arise various problems. This is particularly unfavorable when the liquid medicine is dangerous or otherwise difficult to handle. The backflow prevention structure 4 of this variation is intended to avoid such inconvenience.

Specifically, the backflow prevention structure 4 of this variation is constructed such that a ring 6 made of rubber or synthetic resin as shown in FIG. 8 is fitted around the cylindrical portion 42a of the backflow prevention valve element 42. The inner diameter of this ring 6 is made equal to or slightly smaller than the outer diameter of the cylindrical portion 42a and the outer diameter of the ring 6 is made slightly smaller than the inner diameter of the large-inner-diameter portion 41b of the support cylinder 41. Also, the length of the ring 6 as measured along its inner hole axis is made approximately equal to the length of the cylindrical portion 42a of the backflow prevention valve element 42 along its axial direction.

Figure 9:
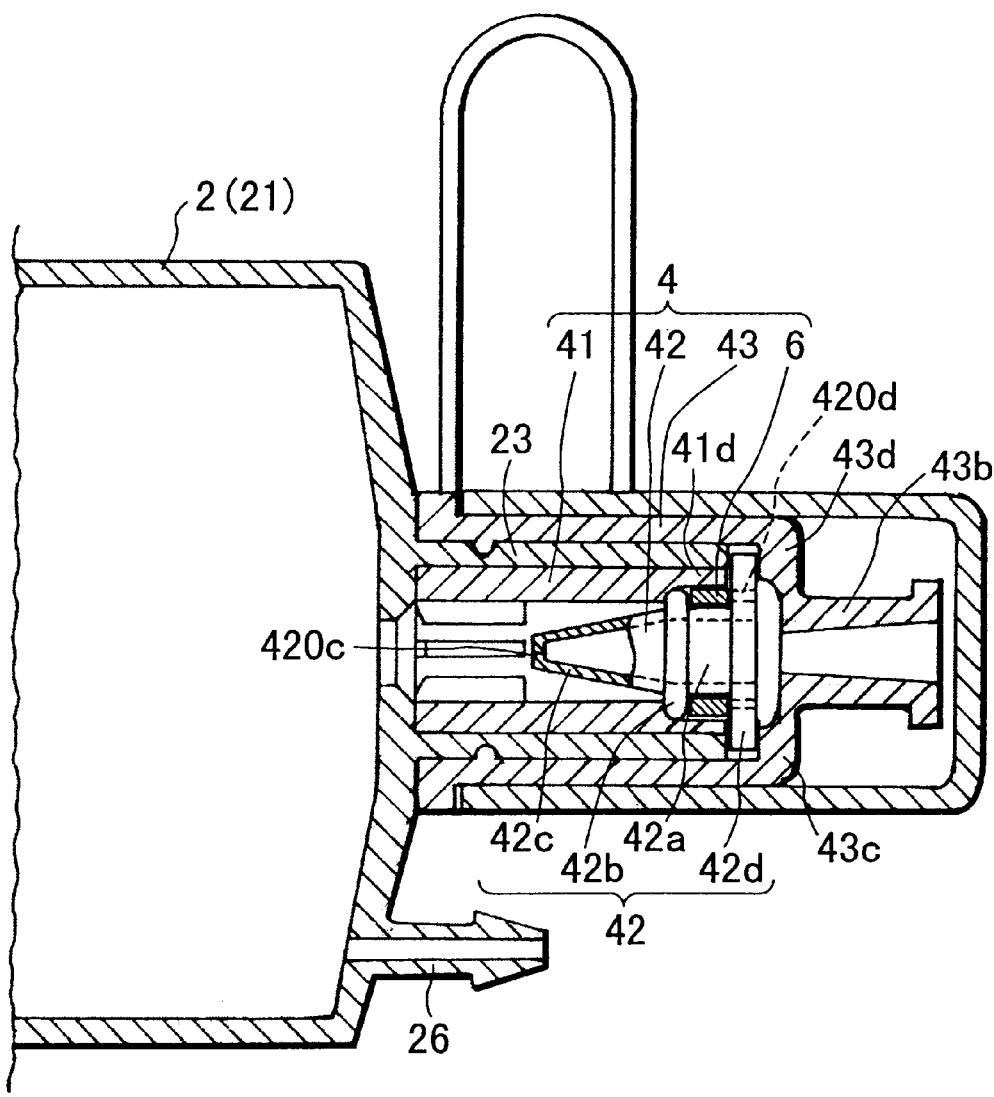
FIG. 9 is a cross-sectional view of the backflow prevention structure of FIG. 8.

According to the backflow prevention structure 4 of this variation, the backflow prevention valve element 42 is inserted into the support cylinder 41 with the ring 6 mounted on the cylindrical portion 42a of the backflow prevention valve element 42 and, then, the tip cover 43 is fitted over the support cylinder 41. Since the ring 6 is fitted in the large-inner-diameter portion 41b of the support cylinder 41 as shown in FIG. 9, the annular valve 42b is held between the ringlike arc-shaped stepped stage 41d of the large-inner-diameter portion 41b and the ring 6. Therefore, even when the pressure within the inlet tube 43b becomes lower than the pressure in the liquid medicine retaining vessel 2, the annular valve 42b does not open to allow backflow of the liquid medicine because it is blocked by the ring 6.

It would be understood from the above discussion that if the ring 6 is previously fitted on the backflow prevention valve element 42, backflow of the liquid medicine from the liquid medicine retaining vessel 2 along the annular valve 42b is prevented even when a patient inserts the injection tube 210 of the injector 200 into the inlet tube 43b of the tip cover 43 and attempts to withdraw the liquid medicine. The backflow prevention structure 4 of this variation serves to reliably prevent problems which may occur when the patient withdraws the liquid medicine from the liquid medicine retaining vessel 2.

Figure 10:
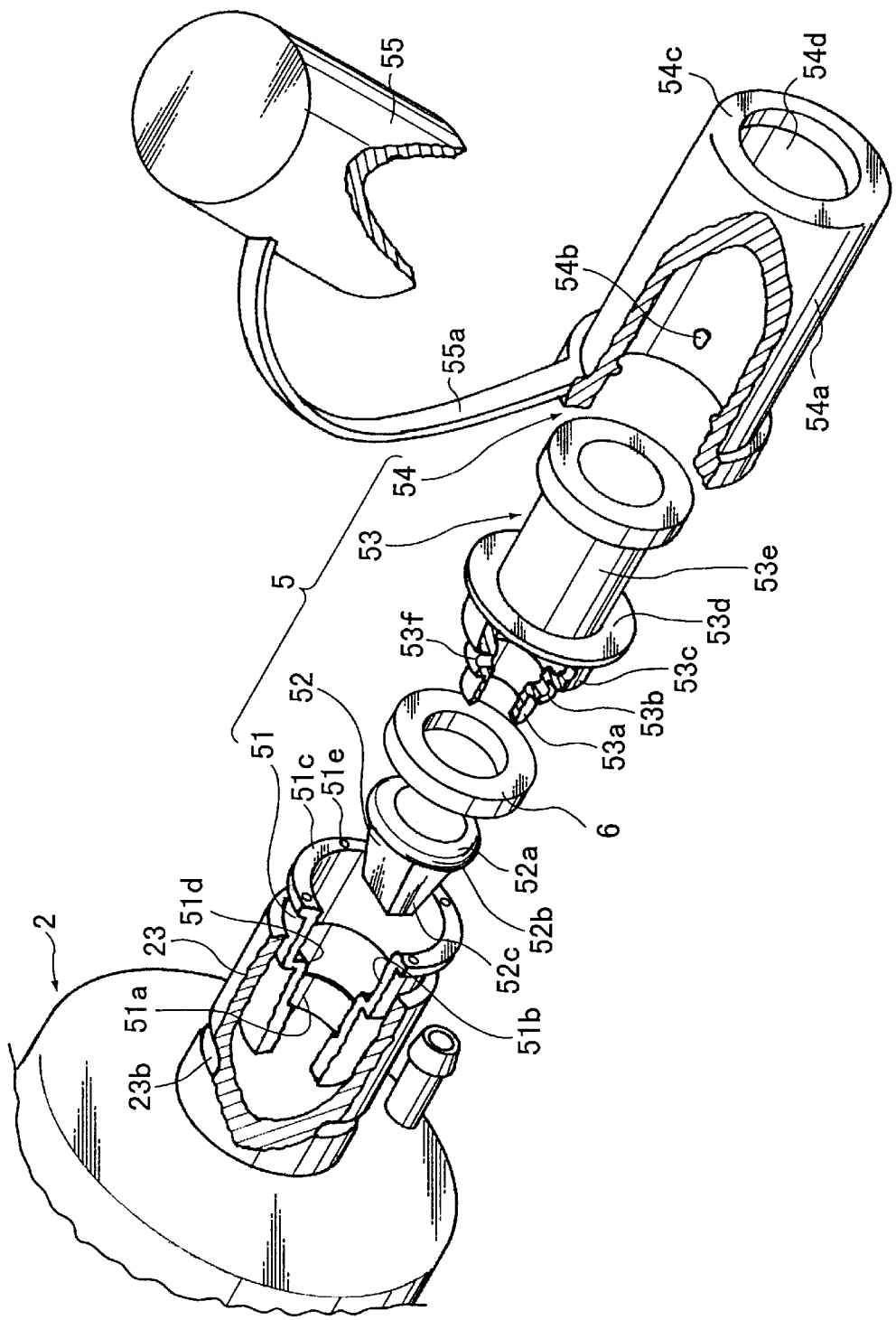
FIG. 10 is a partially cutaway exploded perspective view showing a variation of the backflow prevention structure of the second example shown in FIGS. 6, 7A and 7B.

FIG. 10 is a partially cutaway exploded perspective view showing a variation of the backflow prevention structure 5 of the second example shown in FIGS. 6, 7A and 7B, and FIGS. 11A and 11B are cross-sectional views of the backflow prevention structure 5 of FIG. 10, wherein FIG. 11A is an exploded cross-sectional view and FIG. 11B is a cross-sectional assembly diagram. In this variation, a ring 6 similar to that of the aforementioned variation of the first example (FIG. 8) is fitted around the cylindrical pressing portion 53b of the valve retaining plug 53. The inner diameter of this ring 6 is made equal to or slightly smaller than the outer diameter of the cylindrical pressing portion 53b and the outer diameter of the ring 6 is made approximately equal to the inner diameter of the large-inner-diameter portion 51b of the support cylinder 51. Also, the length of the ring 6 as measured along its inner hole axis is made approximately equal to the length of the cylindrical pressing portion 53b of the valve retaining plug 53 along its axial direction.

According to this variation, the annular valve 52b of the backflow prevention valve element 52 is held between the ringlike arc-shaped stepped stage 51d of the support cylinder 51 and the ring 6 which is fitted around the cylindrical pressing portion 53b of the valve retaining plug 53. Since deformation of the annular valve 52b is prohibited and the bypass holes 53f in the cylindrical pressing portion 53b are blocked in this configuration, backflow of the liquid medicine from the liquid medicine retaining vessel 2 is prevented in a reliable fashion even when the pressure within valve retaining plug 53 upstream of the backflow prevention valve element 52 becomes lower than the pressure in the liquid medicine retaining vessel 2. It would be appreciated from the above discussion that this variation of the second example provides the same advantageous effects as the aforementioned variation of the first example.

Figure 12:
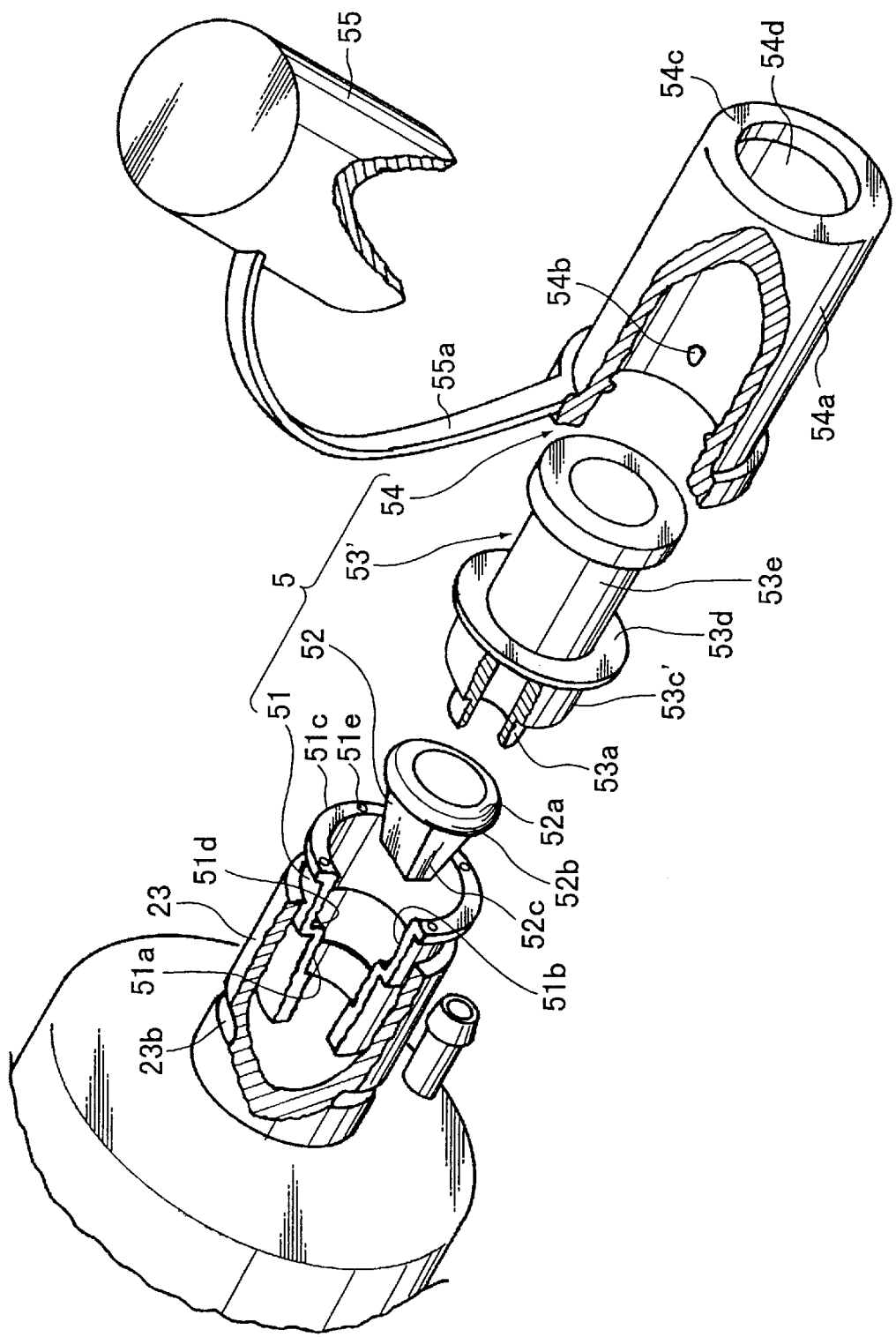
FIG. 12 is a partially cutaway exploded perspective view showing another variation of the backflow prevention structure of the second example shown in FIGS. 6, 7A and 7B.
Figure 13A:
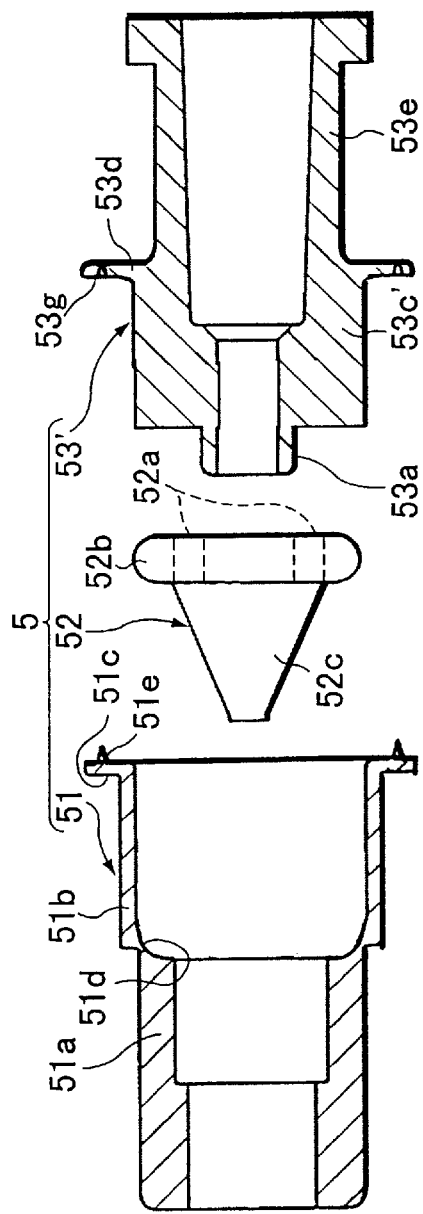
FIGS. 13A and 13B are cross-sectional views of the backflow prevention structure of FIG. 12.
Figure 13B:
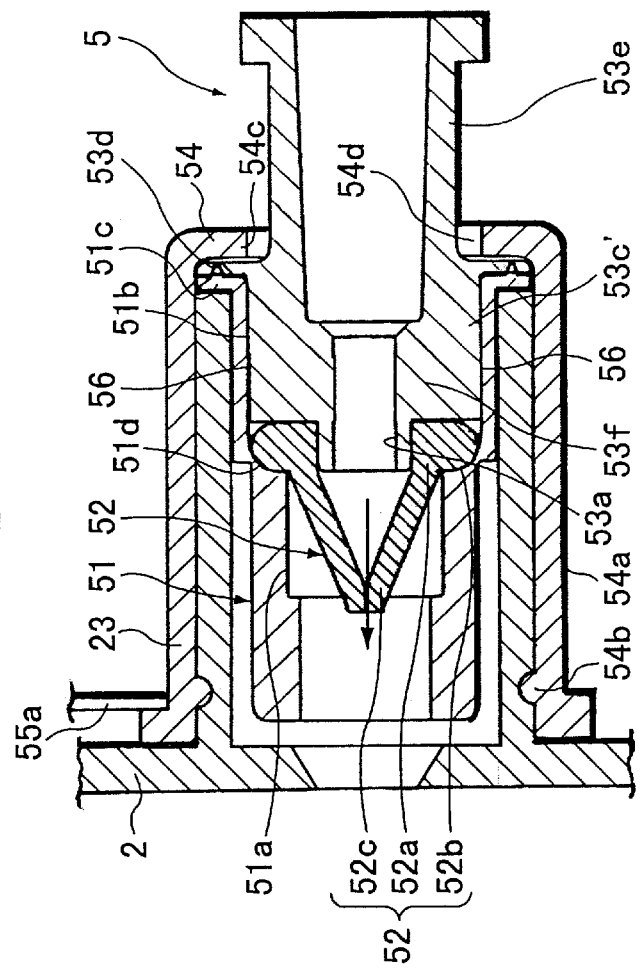
Figure 14A:
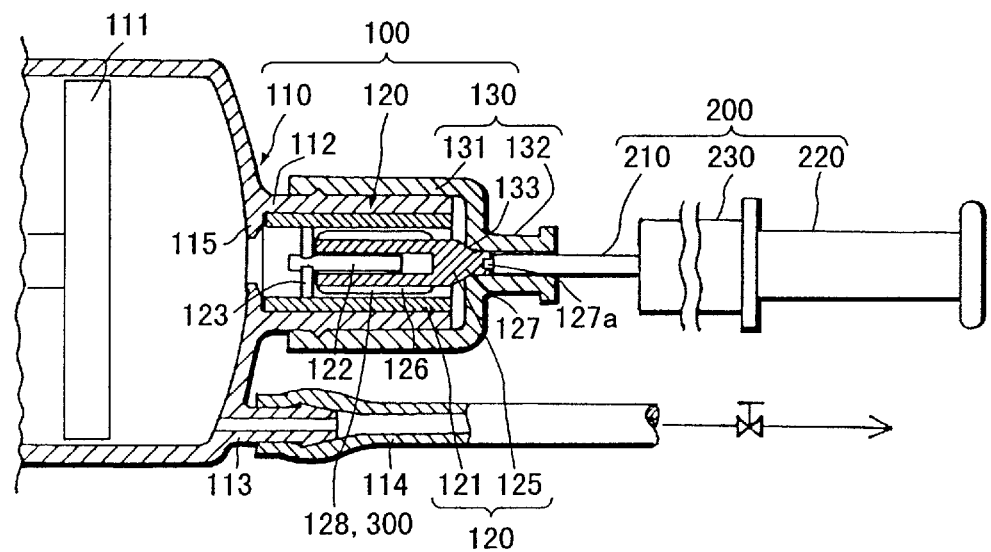
FIGS. 14A and 14B are cross-sectional diagrams illustrating a conventional backflow prevention structure.
Figure 14B:
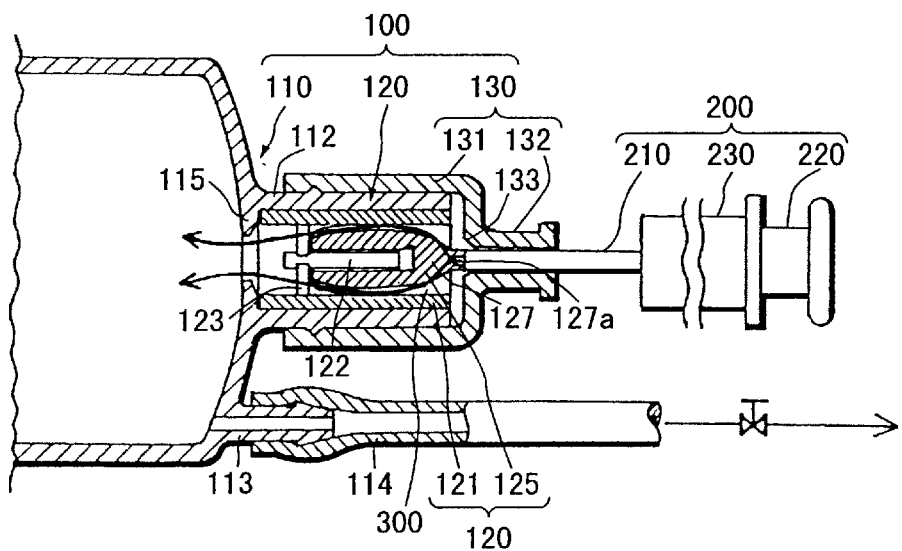

FIG. 12 is a partially cutaway exploded perspective view showing another variation of the backflow prevention structure 5 of the second example shown in FIGS. 6, 7A and 7B, and FIGS. 13A and 13B are cross-sectional views of the backflow prevention structure 5 of FIG. 12, wherein FIG. 13A is an exploded cross-sectional view and FIG. 13B is a cross-sectional assembly diagram. This variation does not employ a ring 6 like the ones used in the aforementioned variations. Instead, the backflow prevention structure 5 of this variation is constructed such that a valve retaining plug 53' itself prohibits deformation of the annular valve 52b of the backflow prevention valve element 52 and thereby prevent backflow of the liquid medicine.

Specifically, the valve retaining plug 53' does not have the cylindrical pressing portion 53b which is provided in the variation shown in FIGS. 10, 11A and 11B. However, a cylindrical plug portion 53c' of the valve retaining plug 53' extends longer toward its tubular connecting portion 53a.

Therefore, when the cylindrical plug portion 53c' is fitted into the support cylinder 51 with the backflow prevention valve element 52 fitted on the tubular connecting portion 53a in a situation shown in FIG. 13A, the annular valve 52b is held between the ringlike arc-shaped stepped stage 51d of the support cylinder 51 and an end surface of the cylindrical plug portion 53c' of the valve retaining plug 53' as shown in FIG. 13B, and this prohibits deformation of the annular valve 52b. It would be appreciated from the above discussion that this variation of the second example provides the same advantageous effects as the aforementioned variations.

It is to be understood that the invention is not limited to the aforementioned specific examples and variations thereof but includes various alternatives and modifications such as those described below.

Although the support cylinder 41 is fitted in the connecting sleeve 23 of the liquid medicine retaining vessel 2 in the aforementioned first example, the connecting sleeve 23 itself may have a small-inner-diameter portion and a large-inner-diameter portion like those of the support cylinder 41 so that the backflow prevention valve element 42 can be fitted into the connecting sleeve 23 without using the support cylinder 41.

Although the backflow prevention valve element 42 is made of silicone rubber in the aforementioned first example, material of the backflow prevention valve element 42 is not limited to silicone rubber in this invention. Other elastic materials, such as synthetic rubber or natural rubber, may be used instead of silicone rubber for making the backflow prevention valve element 42.

While the foregoing discussion has been limited to cases where the backflow prevention structure 4 (5) is attached to the liquid medicine injection device 1, the invention is not limited to such applications. For example, the backflow prevention structure 4 (5) may be used as a backflow prevention unit which is detachably connected at an appropriate point in a liquid medicine carrying channel. In the backflow prevention structure 4 of the first example, this is achieved by combining the support cylinder 41, the backflow prevention valve element 42 and the tip cover 43 into a single unit. Also in the backflow prevention structure 5 of the second example, this is achieved by combining the support cylinder 51, the backflow prevention valve element 52 and the valve retaining plug 53 into a single unit. In either case, the backflow prevention unit thus constructed can be connected at a desired point in a liquid medicine carrying channel if an appropriate unit mounting device is provided in the channel. If the backflow prevention unit is connected upstream of a catheter 11, for instance, in this way, the backflow prevention structure 4 (5) can be made considerably flexible and suited for use in a wide range of situations. For example, it would become possible to regulate injection of the liquid medicine while visually observing symptoms of a patient nearby.

As described above, an inventive backflow prevention structure is connected to a liquid medicine inlet of a liquid medicine injection device for injecting a liquid medicine in a hollow vessel of the liquid medicine injection device into a body part. The structure comprises a backflow prevention valve element provided at the liquid medicine inlet for preventing backflow of the liquid medicine from the hollow vessel. The backflow prevention valve element has first and second valves. The liquid medicine is introduced into the hollow vessel through the first valve, and the liquid medicine in the hollow vessel is allowed to flow in a reverse direction via the second valve when a negative pressure is produced on one side of the backflow prevention valve element opposite to the hollow vessel.

With this backflow prevention structure, the liquid medicine is introduced into the hollow vessel of the liquid medicine injection device through the first valve of the backflow prevention valve element which is fitted in the liquid medicine inlet when the liquid medicine is forced toward the hollow vessel through the liquid medicine inlet by using a specific injection jig. The first and second valves of the backflow prevention valve element prevents backflow of the liquid medicine once injected into the hollow vessel. When a negative pressure is produced on one side of the backflow prevention valve element opposite to the hollow vessel, the liquid medicine once injected into the hollow vessel of the liquid medicine injection device flows in a reverse direction, whereby the liquid medicine in the hollow vessel can be discharged through the liquid medicine inlet.

This backflow prevention structure allows easy liquid medicine filling operation since the backflow prevention valve element prevents backflow of the liquid medicine in a reliable manner when the liquid medicine is injected into the hollow vessel. On the other hand, if the liquid medicine has been overfilled into the hollow vessel, for instance, it can be withdrawn from the hollow vessel by producing a negative pressure in the backflow prevention structure on its side opposite to the backflow prevention valve element by using the injection jig. This structure helps increase labor efficiency when it is required to inject a specified amount of the liquid medicine into the liquid medicine injection device.

The backflow prevention valve element has a cylindrical portion, the first valve is a beaklike nonreturn valve having a slit at a tip end and the second valve is an annular valve bulging outward from around a curved outer surface of the cylindrical portion of the backflow prevention valve element, wherein physical dimensions of the backflow prevention valve element are such that the annular valve comes in contact with a peripheral part of the liquid medicine inlet when the beaklike nonreturn valve is fitted into the liquid medicine inlet, and the annular valve elastically deforms, creating a gap between itself and the peripheral part of the liquid medicine inlet, when a negative pressure Is produced on one side of the backflow prevention valve element opposite to the hollow vessel.

In the backflow prevention structure thus configured, the liquid medicine is introduced into the hollow vessel of the liquid medicine injection device through the slit at the tip end of the beaklike nonreturn valve when the liquid medicine is forced toward the hollow vessel by using the injection jig. Backflow of the liquid medicine once introduced into the hollow vessel is prohibited by the beaklike nonreturn valve and the annular valve which is in tight contact with the peripheral part of the liquid medicine inlet. When a negative pressure is produced on one side of the annular valve opposite to the hollow vessel by using a specific suction jig, the annular valve elastically deforms, creating a gap between itself and the peripheral part of the liquid medicine inlet, so that the liquid medicine once introduced into the hollow vessel can be withdrawn.

With the provision of the backflow prevention valve element having the beaklike nonreturn valve and the annular valve, it becomes possible to provide a simplified backflow prevention structure which satisfies two contradictory requirements of prohibiting backflow of the liquid medicine during injection of the liquid medicine into the liquid medicine injection device and permitting withdrawal of any overfilled liquid medicine through the backflow prevention valve element.

The backflow prevention valve element has a flange which is formed separately from the annular valve at a terminal part of the cylindrical portion of the backflow prevention valve element opposite to the beaklike nonreturn valve, the flange having a larger diameter than the annular valve, a large-inner-diameter portion in which the annular valve is inserted is formed in the liquid medicine inlet, the large-inner-diameter portion having at its innermost part a ringlike stepped stage with which the annular valve comes in contact and the length of the large-inner-diameter portion being such that an inner side surface of the flange comes in contact with an outer end of the large-inner-diameter portion, a bypass hole connecting to a ringlike passage formed between a curved inner surface of the large-inner-diameter portion of the liquid medicine inlet and a curved outer surface of the cylindrical portion of the backflow prevention valve element is made in the flange, and a tip cover having at its central part an inlet tube which serves as a passage of the liquid medicine is fitted on the liquid medicine inlet wherein the tip cover presses the flange against the liquid medicine inlet without closing the bypass hole.

In the backflow prevention structure thus configured, the liquid medicine injected from the inlet tube is introduced into the hollow vessel of the liquid medicine injection device through the cylindrical portion of the backflow prevention valve element with backflow of the liquid medicine prohibited by the annular valve. On the other hand, when a negative pressure is produced in the inlet tube by using the suction jig, the annular valve which has been in contact with the ringlike stepped stage elastically deforms due to the negative pressure, creating a gap between its curved outer surface and the curved inner surface of the large-inner-diameter portion, so that the liquid medicine in the hollow vessel passes through this gap and is discharged to the exterior through the ringlike passage formed between the curved inner surface of the large-inner-diameter portion of the liquid medicine inlet and the curved outer surface of the cylindrical portion of the backflow prevention valve element and through the bypass hole in the flange.

Since there is formed a space which allows elastic deformation of the annular valve between the flange and the annular valve by forming the flange on the cylindrical portion of the backflow prevention valve element apart from the annular valve, there is formed a backflow passage connected to the ringlike passage when a negative pressure is produced in the inlet tube. Consequently, the liquid medicine in the hollow vessel of the liquid medicine injection device is allowed to flow in the reverse direction in a reliable manner.

A large-inner-diameter portion in which the annular valve is inserted is formed in the liquid medicine inlet, the large-inner-diameter portion having at its innermost part a ringlike stepped stage with which the annular valve comes in contact, a valve retainer for pressing the cylindrical portion of the backflow prevention valve element such that the annular valve comes in contact with the ringlike stepped stage is fitted into the large-inner-diameter portion of the liquid medicine inlet, the valve retainer having a liquid medicine injecting hole made on its central axis, a cylindrical pressing portion whose diameter is smaller than that of the large-inner-diameter portion with which a terminal part of the cylindrical portion of the backflow prevention valve element comes in contact, and a plug portion whose outer diameter is such that it can fit into the large-inner-diameter portion of the liquid medicine inlet in sliding contact, a bypass hole connecting a ringlike passage formed between a curved outer surface of the cylindrical pressing portion of the valve retainer and a curved inner surface of the large-inner-diameter portion of the liquid medicine inlet to the liquid medicine injecting hole is made in the valve retainer, and a tip cover having at its central part a passage hole which serves as a passage of the liquid medicine is fitted on the liquid medicine inlet, wherein the tip cover presses the cylindrical pressing portion of the valve retainer against the cylindrical portion of the backflow prevention valve element without closing the liquid medicine injecting hole.

In the backflow prevention structure thus configured, the liquid medicine injected from the passage hole is introduced into the hollow vessel of the liquid medicine injection device through the cylindrical portion of the backflow prevention valve element with backflow of the liquid medicine prohibited by the annular valve. On the other hand, when a negative pressure is produced in the valve retainer by using the suction jig, the annular valve which has been in contact with the ringlike stepped stage elastically deforms due to the negative pressure, creating a gap between its curved outer surface and the curved inner surface of the large-inner-diameter portion, so that the liquid medicine in the hollow vessel passes through this gap and is discharged to the exterior through the ringlike passage formed between the cylindrical pressing portion of the valve retainer and the large-inner-diameter portion of the liquid medicine inlet and through the bypass hole in the valve retainer and the liquid medicine injecting hole.

Since the valve retainer presses against the cylindrical portion of the backflow prevention valve element where the annular valve is formed as described above, there is formed a space which allows elastic deformation of the annular valve between the curved outer surface of the cylindrical pressing portion of the valve retainer and the curved inner surface of the large-inner-diameter portion of the liquid medicine inlet. As a result, there is formed a backflow passage connected to the ringlike passage when a negative pressure is produced in the valve retainer, and the liquid medicine in the hollow vessel of the liquid medicine injection device is allowed to flow in the reverse direction in a reliable manner. Furthermore, since it is not necessary to form a flange on the cylindrical portion of the backflow prevention valve element, its construction is simplified, and it becomes possible to reduce material and production costs of the backflow prevention valve element which is a consumable.

In any of the aforementioned backflow prevention structures, a backflow prevention member for preventing backflow of the liquid medicine via the second valve may be detachably fitted to the liquid medicine inlet.

In the backflow prevention structure thus configured, deformation of the second valve is prohibited by the backflow prevention member even when the pressure in the backflow prevention structure on its side opposite to the hollow vessel is made lower than the pressure in the hollow vessel by suction. Therefore, backflow of the liquid medicine is prevented in a reliable manner.

Further, an inventive backflow prevention unit to be connected in a liquid medicine carrying channel for injecting a liquid medicine into a body part comprises a support cylinder to be fitted into the liquid medicine carrying channel in tight contact with its curved inner surface, the support cylinder having a large-inner-diameter portion on an inflow side and an adjoining small-inner-diameter portion, and a backflow prevention valve element which is fitted into the support cylinder from its inflow side, wherein the backflow prevention valve element has a cylindrical portion which is fitted into the large-inner-diameter portion of the support cylinder, a beaklike nonreturn valve which is formed integrally with the cylindrical portion and fitted into the small-inner-diameter portion of the support cylinder, and an annular valve bulging outward from around a curved outer surface of the cylindrical portion of the backflow prevention valve element, the outer diameter of the annular valve being larger than the diameter of the small-inner-diameter portion of the support cylinder, wherein a slit which opens only when the liquid medicine flows in a normal direction is formed in the beaklike nonreturn valve, wherein the annular valve is shaped such that it comes in contact with a ringlike stepped stage formed between the small-inner-diameter portion and the large-inner-diameter portion when the backflow prevention valve element is fitted into the small-inner-diameter portion, and wherein the annular valve elastically deforms, creating a gap between itself and a peripheral part of a liquid medicine inlet, when a negative pressure is produced on one side of the backflow prevention valve element opposite to the body part.

The backflow prevention unit thus constructed provides the same advantageous effects as the aforementioned backflow prevention structures. Furthermore, the backflow prevention unit can be connected at an appropriate point in the liquid medicine carrying channel. Thus, if the backflow prevention unit is connected upstream of a catheter, for instance, it is possible to regulate injection of the liquid medicine while visually observing symptoms of a patient nearby. The backflow prevention structure can be made considerably flexible and suited for use in a wide range of situations when its constituent elements are combined into a single unit in this fashion.

In this backflow prevention unit, a backflow prevention member for preventing backflow of the liquid medicine via the annular valve may be detachably fitted in the support cylinder.

In the backflow prevention unit thus constructed, deformation of the annular valve is prohibited by the backflow prevention member even when the pressure in the backflow prevention unit on one side of the backflow prevention valve element opposite to the body part is made lower than the pressure in the hollow vessel by suction. Therefore, backflow of the liquid medicine is prevented in a reliable manner.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A backflow valve structure which is to be connected to a liquid medicine inlet of a liquid medicine injection device for injecting a liquid medicine in a hollow vessel of the liquid medicine injection device into a body part, the backflow valve structure comprising:

a backflow valve element provided within the liquid medicine inlet, the backflow valve element including:
a first valve for introducing the liquid medicine into the hollow vessel along a first direction; and
a second valve for allowing the liquid medicine in the hollow vessel to flow in a direction opposite to the first direction when a negative pressure is produced on one side of the backflow valve element opposite to the hollow vessel.

2. The backflow prevention structure according to claim 1, wherein a backflow prevention member for preventing backflow of the liquid medicine via the second valve is detachably fitted to the liquid medicine inlet.

3. A backflow valve structure which is to be connected to a liquid medicine inlet of a liquid medicine injection device for injecting a liquid medicine in a hollow vessel of the liquid medicine injection device into a body part, the backflow valve structure comprising:

a backflow valve element provided within the liquid medicine inlet, the backflow valve element including:
a first valve for introducing the liquid medicine into the hollow vessel along a first direction; and
a second valve for allowing the liquid medicine in the hollow vessel to flow in a direction opposite to the first direction when a negative pressure is produced on one side of the backflow valve element opposite to the hollow vessel,
wherein the backflow valve element has a cylindrical portion, the first valve is a beaklike nonreturn valve having a slit at a tip end and the second valve is an annular valve bulging outward from around a curved outer surface of the cylindrical portion of the backflow valve element, and wherein physical dimensions of the backflow valve element are such that the annular valve comes in contact with a peripheral part of the liquid medicine inlet when the beaklike nonreturn valve is fitted into the liquid medicine inlet, and the annular valve elastically deforms, creating a gap between itself and the peripheral part of the liquid medicine inlet, when a negative pressure is produced on one side of the backflow valve element opposite to the hollow vessel.

4. The backflow prevention structure according to claim 3, wherein a backflow prevention member for preventing backflow of the liquid medicine via the second valve is detachably fitted to the liquid medicine inlet.

5. The backflow prevention structure according to claim 3, wherein the backflow prevention valve element has a flange which is formed separately from the annular valve at a terminal part of the cylindrical portion of the backflow prevention valve element opposite to the beaklike nonreturn valve, the flange having a larger diameter than the annular valve, a large-inner-diameter portion in which the annular valve is inserted is formed in the liquid medicine inlet, the large-inner-diameter portion having at its innermost part a ringlike stepped stage with which the annular valve comes in contact and the length of the large-inner-diameter portion being such that an inner side surface of the flange comes in contact with an outer end of the large-inner-diameter portion, a bypass hole connecting to a ringlike passage formed between a curved inner surface of the large-inner-diameter portion of the liquid medicine inlet and a curved outer surface of the cylindrical portion of the backflow prevention valve element is made in the flange, and a tip cover having at its central part an inlet tube which serves as a passage of the liquid medicine is fitted on the liquid medicine inlet wherein the tip cover presses the flange against the liquid medicine inlet without closing the bypass hole.

6. The backflow prevention structure according to claim 5, wherein a backflow prevention member for preventing backflow of the liquid medicine via the second valve is detachably fitted to the liquid medicine inlet.

7. The backflow prevention structure according to claim 3, wherein a large-inner-diameter portion in which the annular valve is inserted is formed in the liquid medicine inlet, the large-inner-diameter portion having at its innermost part a ringlike stepped stage with which the annular valve comes in contact, a valve retainer for pressing the cylindrical portion of the backflow prevention valve element such that the annular valve comes in contact with the ringlike stepped stage is fitted into the large-inner-diameter portion of the liquid medicine inlet, the valve retainer having a liquid medicine injecting hole made on its central axis, a cylindrical pressing portion whose diameter is smaller than that of the large-inner-diameter portion with which a terminal part of the cylindrical portion of the backflow prevention valve element comes in contact, and a plug portion whose outer diameter is such that it can fit into the large-inner-diameter portion of the liquid medicine inlet in sliding contact, a bypass hole connecting a ringlike passage formed between a curved outer surface of the cylindrical pressing portion of the valve retainer and a curved inner surface of the large-inner-diameter portion of the liquid medicine inlet is made in the valve retainer, and a tip cover having at its central part a passage hole which serves as a passage of the liquid medicine is fitted on the liquid medicine inlet, wherein the tip cover presses the cylindrical pressing portion of the valve retainer against the cylindrical portion of the backflow prevention valve element without closing the liquid medicine injecting hole.

8. The backflow prevention structure according to claim 7, wherein a backflow prevention member for preventing backflow of the liquid medicine via the second valve is detachably fitted to the liquid medicine inlet.

9. A backflow prevention unit to be connected in a liquid medicine carrying channel for injecting a liquid medicine into a body part, the backflow prevention unit comprising:

a support cylinder to be fitted into the liquid medicine carrying channel in tight contact with its curved inner surface, the support cylinder having a large-inner-diameter portion on an inflow side and an adjoining small-inner-diameter portion; and
a backflow prevention valve element which is fitted into the support cylinder from its inflow side;

wherein the backflow prevention valve element has a cylindrical portion which is fitted into the large-inner-diameter portion of the support cylinder, a beaklike nonreturn valve which is formed integrally with the cylindrical portion and fitted into the small-inner-diameter portion of the support cylinder, and an annular valve bulging outward from around a curved outer surface of the cylindrical portion of the backflow prevention valve element, the outer diameter of the annular valve being larger than the diameter of the small-inner-diameter portion of the support cylinder;

wherein a slit which opens only when the liquid medicine flows in a normal direction is formed in the beaklike nonreturn valve;

wherein the annular valve is shaped such that it comes in contact with a ringlike stepped stage formed between the small-inner-diameter portion and the large-inner-diameter portion when the backflow prevention valve element is fitted into the small-inner-diameter portion; and wherein the annular valve elastically deforms, creating a gap between itself and a peripheral part of a liquid medicine inlet, when a negative pressure is produced on one side of the backflow prevention valve element opposite to the body part.

10. The backflow prevention unit according to claim 9, wherein a backflow prevention member for preventing backflow of the liquid medicine via the annular valve is detachably fitted in the support cylinder.

11. The backflow prevention structure according to claim 1, wherein the first valve and the second valve are integrally formed with each other.

12. The backflow prevention structure according to claim 11, wherein the backflow prevention element further including:

a cylindrical support portion provided within the liquid medicine inlet to accommodate the first valve and the second valve, the cylindrical support portion having a plurality of ribs parallel to an axis of the cylindrical support portion.

13. A backflow valve structure in combination with a liquid medicine injection device for injecting a liquid medicine in a hollow vessel of the liquid medicine injection device into a body part, the liquid medicine injection device having a liquid medicine inlet, the backflow valve structure comprising:

a backflow valve element provided within the liquid medicine inlet, the backflow valve element including:
a first valve for introducing the liquid medicine into the hollow vessel along a first direction; and
a second valve for allowing the liquid medicine in the hollow vessel to flow in a direction opposite to the first direction when a negative pressure is produced on one side of the backflow valve element opposite to the hollow vessel.

14. A backflow valve structure in combination with a liquid medicine injection device as claimed in claim 13, wherein the backflow valve element has a cylindrical portion, the first valve is a beaklike nonreturn valve having a slit at a tip end and the second valve is an annular valve bulging outward from around a curved outer surface of the cylindrical portion of the backflow valve element, and wherein physical dimensions of the backflow valve element are such that the annular valve comes in contact with a peripheral part of the liquid medicine inlet when the beaklike nonreturn valve is fitted into the liquid medicine inlet, and the annular valve elastically deforms, creating a gap between itself and the peripheral part of the liquid medicine inlet, when a negative pressure is produced on one side of the backflow valve element opposite to the hollow vessel.

* * * * *